United States Patent [19]
Jew et al.

[11] Patent Number: 5,834,437
[45] Date of Patent: Nov. 10, 1998

[54] ASIATIC ACID DERIVATIVES ITS MANUFACTURING METHOD AND DERMATOLOGICAL AGENT CONTAINING IT

[75] Inventors: Sang-Sup Jew; Hee-Doo Kim, both of Seoul; Young-Hoon Jung, Kyunggi; Eun-Hee Park, Seoul; Sung-Ki Seo, Pusan; Tae-Gyu Nam, Chungbuk; Duc-Ky Hahn, Seoul; Jae-Ho Park, Seoul; Pil-Jong Sim, Seoul; Min-Jung Lim, Seoul; Kyung-Haw Lim, Seoul, all of Rep. of Korea

[73] Assignee: Dong Kook Pharmaceutical Co., Ltd., Rep. of Korea

[21] Appl. No.: 566,130

[22] Filed: Dec. 1, 1995

[30] Foreign Application Priority Data

Dec. 3, 1994 [KR] Rep. of Korea ................. 1994-32697

[51] Int. Cl.$^6$ ............................ A61K 31/70; C07H 15/24

[52] U.S. Cl. ............................... 514/25; 514/23; 514/766; 536/4.1; 536/18.1; 562/498

[58] Field of Search ............................ 562/498; 514/766, 514/23, 25; 536/4.1, 18.1

[56] References Cited

FOREIGN PATENT DOCUMENTS 0 383 171 A2  8/1990  European Pat. Off. .

*Primary Examiner*—Elli Peselev
*Attorney, Agent, or Firm*—Gary M. Nath; Suet M. Chong; Nath & Associates

[57] ABSTRACT

The object of the present invention is to provide asiatic acid derivatives, its pharmaceutically acceptable salts or esters.

Asiatic acid, its trisaccharide asiaticoside and mddecassic acid, extracted from *Centella asiatica* have been used for a long time in the management of skin scars and chronic ulcers. In this invention, asiatic acid derivatives synthesized from asiatic acid show excellent wound-healing properties.

4 Claims, No Drawings

ASIATIC ACID DERIVATIVES ITS MANUFACTURING METHOD AND DERMATOLOGICAL AGENT CONTAINING IT

FIELD OF THE INVENTION

This invention relates to asiatic acid derivatives expressed by the following chemical formula, and its pharmaceutically acceptable salt or ester, its manufacturing method and dermatological agent containing it.

(I)

Wherein;

$R^1$ is selected from the group consisting of hydrogen, hydroxy which may be protected by acetyl or benzyl, methyl, ethyl, methoxy, ethoxy, vinyl, ethynyl, cyano, azaide, methanesulfonyloxy, phenylthio, or (methylthio) thiocarbonyloxy;

$R_2$ is selected from the group consisting of hydrogen, hydroxy which may be protected by acetyl or benzyl, methoxy, or ethoxy;

$R_1$ and $R_2$ may form oxo altogether;

$R_3$ is selected from the group consisting of hydrogen, hydroxy which may be protected by acetyl or benzyl, vinyl, methyl, or ethyl;

$R_4$ is selected from the group consisting of hydrogen, methyl, ethyl, vinyl, or hydroxy which may be protected by acetyl or benzyl;

$R_2$ and $R_4$ may form epoxy altogether;

$R_3$ and $R_4$ may form oxo altogether;

$R_5$ is selected from the group consisting of methyl, hydroxymethyl where hydroxy may be protected by acetyl or benzyl, tert-butyldimethylsilyloxymethyl, carboxyl, carboxylester, carboxylamide, or aldehyde;

$R_4$ and $R_5$ may form $-OC(CH_3)_2OCH_2-$ altogether;

$R_6$ is selected from the group consisting of hydrogen, or methyl;

$R_7$ is selected from the group consisting of $-CH_2COOR$ or $-COOR$ [hence, R is hydrogen, methyl, $CH(OR_9)R_8$, and $CH(OR_{11})CH_2R_{10}$ ($R_8$ is selected from the group consisting of hydrogen, methyl or ethyl;

$R_9$ is selected from the group consisting of methyl, ethyl, octyl, benzyl, methoxymethyl, or methoxyethyl;

$R_{10}$ is selected from the group consisting of hydrogen, methyl or ethyl;

$R_{10}$ and $R_{11}$ may be associated to form $-CH_2CH_2CH_2-$, glucosyl or rhamnosyl where hydroxy may be protected by acetyl or benzyl], hydroxymethyl where hydroxy may be protected by acetyl or benzyl, methanesulfony-loxymethyl, or cyanomethyl;

$R_2$ and $R_{13}$ represent hydrogen, respectively, or oxo altogether. [When $R_1$, $R_2$, $R_3$, $R_4$, $R_5$ and $R_6$ represent hydroxy, hydrogen, hydrogen, hydroxy, hydroxymethyl and methyl, respectively, R is not hydrogen or methyl and $R_8$ is not hydrogen; In case where $R_1$ is hydroxy, $R_2$ is hydrogen, $R_3$ & $R_4$ form $-OC(CH_3)_2OCH_2-$ together with $R_5$ and $R_6$ is methyl, R is not methyl.]

DESCRIPTION OF THE PRIOR ART

Asiatic acid, its trisaccharide asiaticoside and madecassic acid are extracted from *Centella asiatica*. They were first separated by Bontems et al. in 1941 [J. E. Bontems, Bull. Sci. Pharmacol., 49, 186–91 (1941)] and their structures were also disclosed by Polonsky et al. [J. Polonsky, Compt. Rend., 232, 1878–80(1951); J. Polonsky, Bull. Soc. Chim., 173–80(1953)].

*Centella asiatica* extracts containing asiatic acid and asiaticoside have been for a long time used in the management of skin scars and chronic ulcers. Said extracts have also used in the treatment of skin deformity owing to tuberculosis and leprosy [P. Boiteau, A. Buzas, E. Lederer and J. Polonsky, Bull. Soc. Chim., 31, 46–51 (1949)]. The pharmacological mode of action related to said substances' wound-healing properties has been reportedly said to activate malpighean cells and induce keratinization [May. Anne, Eur. J. Pharmacol., 4(3), 331–9 (1968)].

Madecassol, one of the currently marketed dermatological agents is also a mixture of three compounds containing asiaticoside (40%) plus asiatic acid and madecassic acid (60%). Among them, asiaticoside, trisaccharide of asiatic acid, has reportedly demonstrated main efficacy while asiatic acid itself has produced no efficacy (Kiesswetter, Wien. Med. Wochschr., 114(7), 124–6 (1964)]. However, there have been some reports that since the efficacy mechanism of said substances depends on their absorption in the body, asiatic acid itself proved to have exhibited the actual efficacy [L. F. Chasseaud, B. J. Fry, D. R. Hawkins, J. D. Lewis, T. Taylor ard D. E. Hathway, Arzneim-Forsch, 21(9), 179–84 (1971)]. Thus, the synthesis and pharmacological mechanism of asiatic acid derivatives have drawn considerable interest. However, the total synthesis of asiatic acid from simple starting material has recognized some disadvantages in that a lot of process steps are inevitably made, thus require significant manufacturing costs.

SUMMARY OF THE INVENTION

To overcome these shortcomings, the inventor et al. have successfully synthesized various asiatic acid derivatives by using asiatic acid obtained from *Centella asiatica* as a starting material and noted that said derivatives have excellent wound-healing properties so that the present invention was completed.

DETAILED DESCRIPTION OF THE INVENTION

The process of manufacturing asiatic acid derivatives according to the present invention is described as set forth hereunder.

Process 1

To perform the molecular modification on the OH at 2 position of asiatic acid, asiatic acid is treated with diazomethane to yield methylasiatate (2b) quantitatively and again treated with p-toluenesulfonic acid (PTSA) in acetone solvents, to prepare methyl 3,23-O-isopropylidene asiatate (3) where 3,23-OH is protected. The unreacted starting material is recovered. Further, the protected methylasiatate (3) is oxidized by piridinium dichromate (PDC) and acetic anhydride to afford methyl 2-oxo-3,23-O-isopropylidene asiatate (4, R=methyl). The resulting compound is treated with PTSA in methanol solvents, to yield methyl 2-oxoasiatate (5,R=methyl)

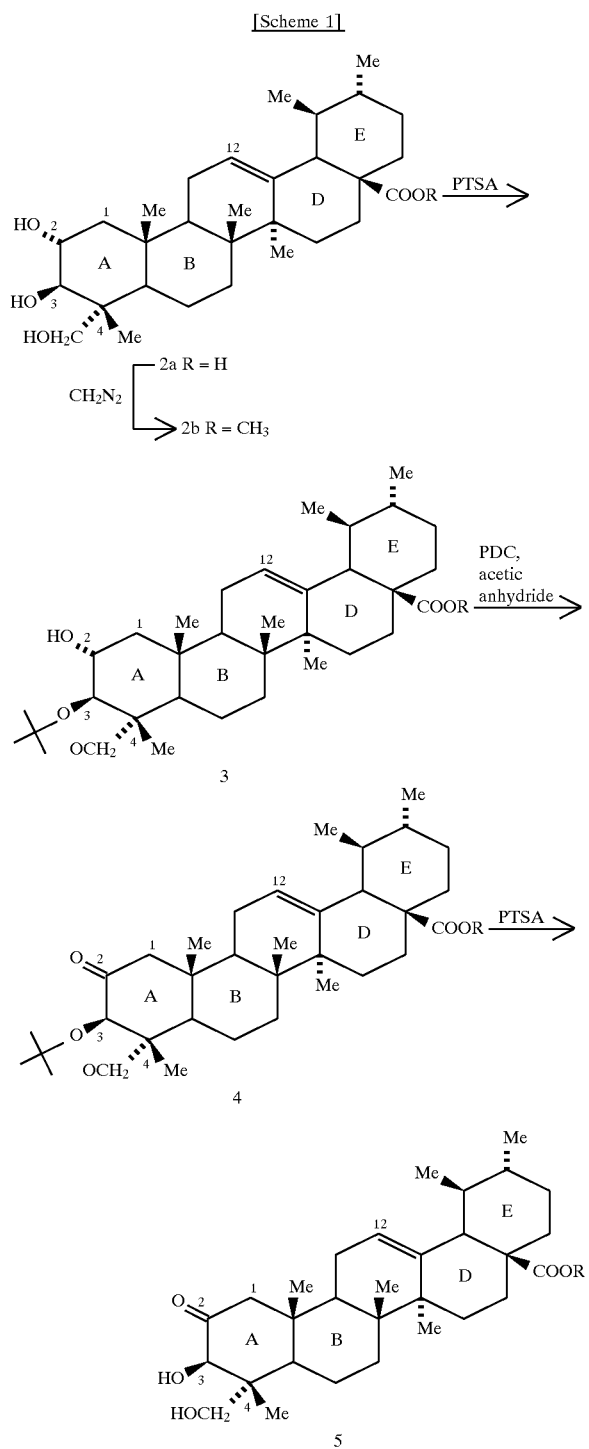

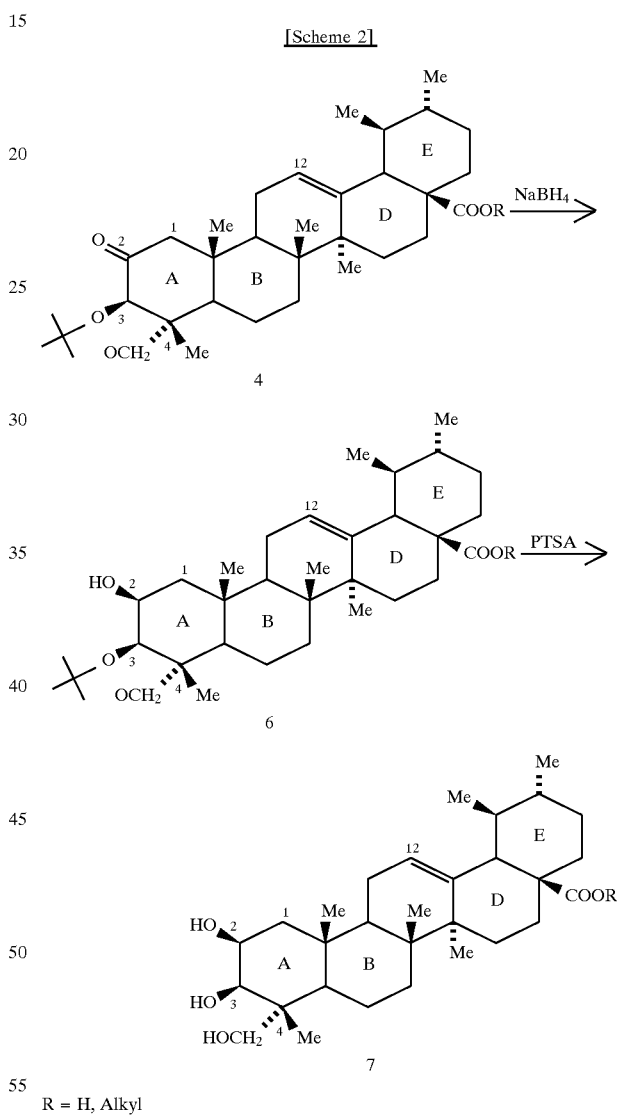

In the same synthesis procedure using asiatic acid (2a), 3,23-O-isopropylidene asiatic acid (3, R=H) and 2-oxo-3, 23-O-isopropylidene asiatic acid (4, R=H) is yielded, respectively. Said compound (4, R=H) is treated with PTSA to prepare methyl 2-oxo-asiatic acid (5, R=H) [Scheme 1].

When R [said Scheme 1] is hydrogen and alkyl, respectively, both oxidation and deprotecting reactions show that the yield in R=hydrogen is lower than R=alkyl. Accordingly, in case of manufacturing a compound (R=hydrogen), it is rather desirable that a compound (R=alkyl) should be prepared and hydrolyzed.

Process 2

Further, said prepared compound (4, R=alkyl) is reduced with sodium borohydride to prepare methyl 2β, hydroxy-3β, 23-isopropylidendioxyurs-12-ene-28-oate (6, R=alkyl), a novel compound of the present invention. Then, said compound (6, R=alkyl) is treated with PTSA to prepare methyl 2β, 3β, 23-trihydroxyurs-12-ene-28-oate(7, R=alkyl), another novel compound of the present invention [Scheme 2]. Even in case of a compound (4, R=H), the same reaction is made so that a compound of the present invention (6,7) representing R=hydrogen is yielded.

Process 3

Also, 2α-alkyl-3,23-O-isopropylidene asiatic acid (17) is prepared by Grignard reaction of the compound (4, R=H) of the present invention with R'MgBr(R'=-methyl, ethyl, vinyl, ethynyl, and cyano), followed by deprotecting reaction of compound(17) to yield 2α-alkylasiatic acid (18), another compound of the present invention [Scheme 3].

[Scheme 3]

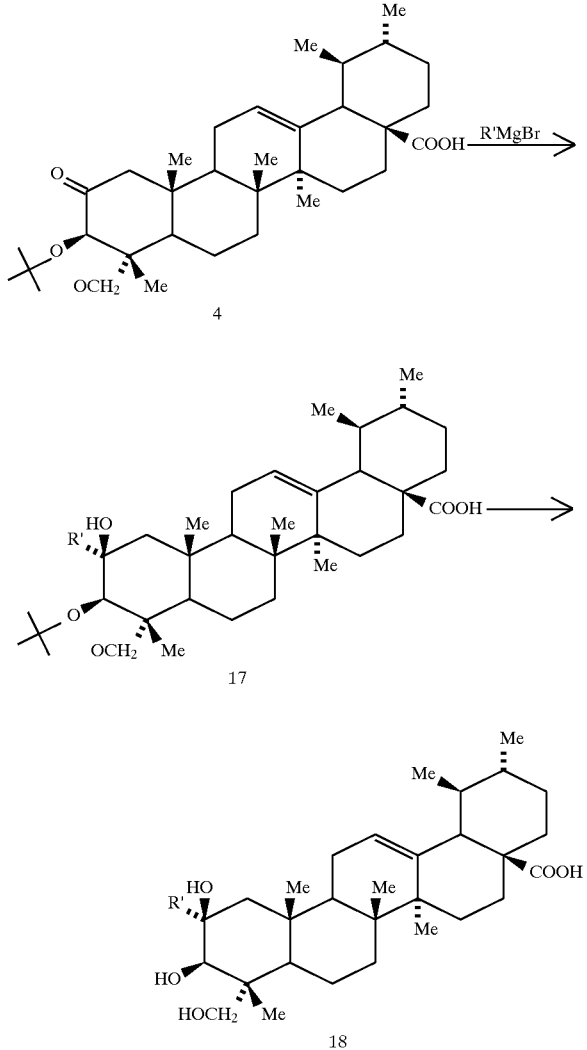

[Scheme 4]

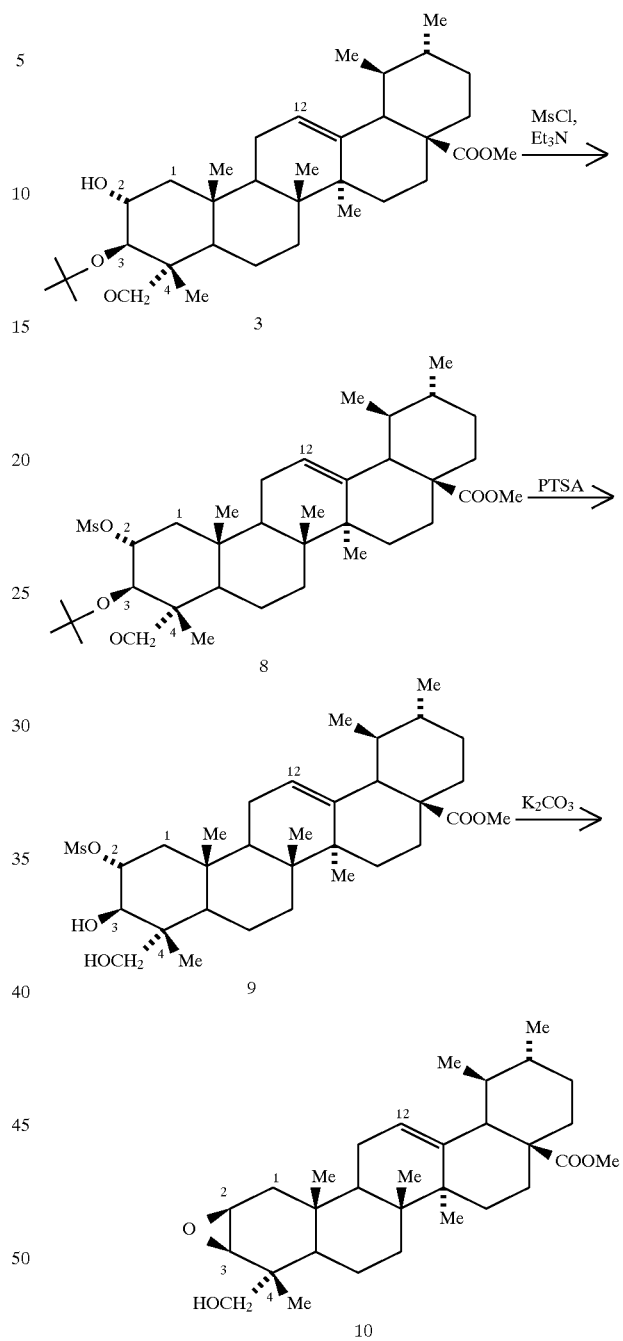

Process 4

Meantime, in order to introduce various substituents at 2,3 positions of asiatic acid, the 2,3-hydroxy is converted to 2,3-epoxy and via reactions with various nucleophiles for the clevage of epoxy, a series of novel compounds of the present invention may be made available. In other words, methanesulfonylchloride and triethylamine are added to said prepared methyl 3,23-O-isopropylidene asiatate (3) to give methyl 2-methanesulfonyl-3,23-O-isopropylidene asiatate (8), one compound(8) of the present invention. Then, said compound is treated with PTSA to prepare methyl 2-methanesulfonyl asiatate (9), one compound of the present invention. The resulting compound is again treated with potassium carbonate in methanol solvents to synthesize methyl 2β,3β-epoxy-23-hydroxyurs-12-ene-28-oate(10), one compound of the present invention [Scheme 4].

Process 5

Also, the inventor et al. discover that when epoxy-cyclohexane, having the same strong bonding forces as said prepared compound (10), is reacted with metal hydrides, especially lithium aluminum hydride(LAH), LAH proceeded generally via the axial attack by the stereoelectronic controlling or after its preferential bonding with surrounding hydroxy groups, LAH proceeded via intramolecular attack to form 2β-alcohol. Accordinlgy, compound (10) is treated with LAH to prepare 2β, 3β-epoxyurs-12-ene-23, 28-diol (11) where ester sites are reduced and 3-deoxyasiatic alcohol (12) where ester sites and epoxy are reduced. Through the prolonged time of such reaction, the compound(12) is prepared in high yield [Scheme 5].

[Scheme 5]

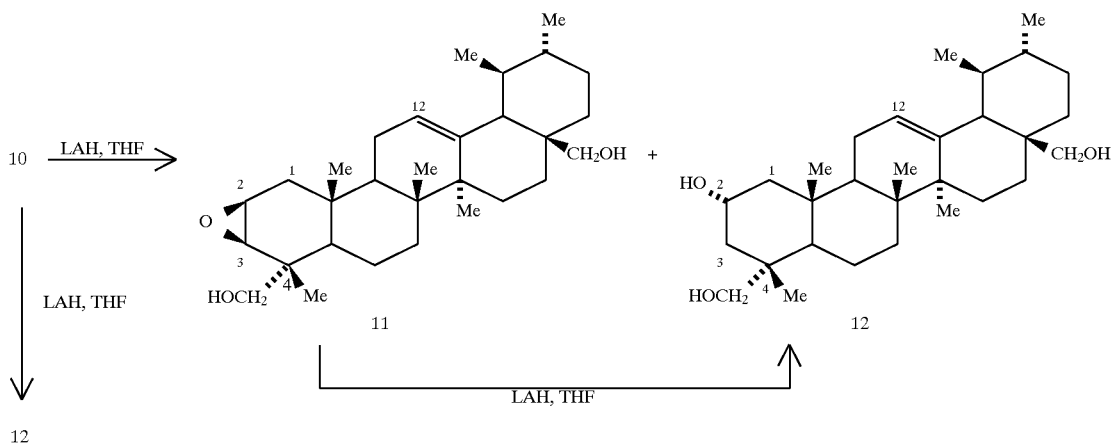

Process 6

Said compounds (11,12) are also made available by the following process: Compound (10) is treated with tert-butyldimethylsilyl chloride and imidazole in dimethylformamide solvents to give the intermediate compound (13) quantitatively. Said compound is refluxed to reduce epoxide and is again desilylated with tetrabutylammonium fluoride [Scheme 6].

[Scheme 6]

Process 7

Also, the compound (10) is reacted with diborane and catalytic amounts of sodium borohydride to prepare methyl 2-deoxyasiatate (14) and methyl 3-deoxyasiatate (15), one compound of the present invention [scheme 7].

[Scheme 7]

-continued

[Scheme 7]

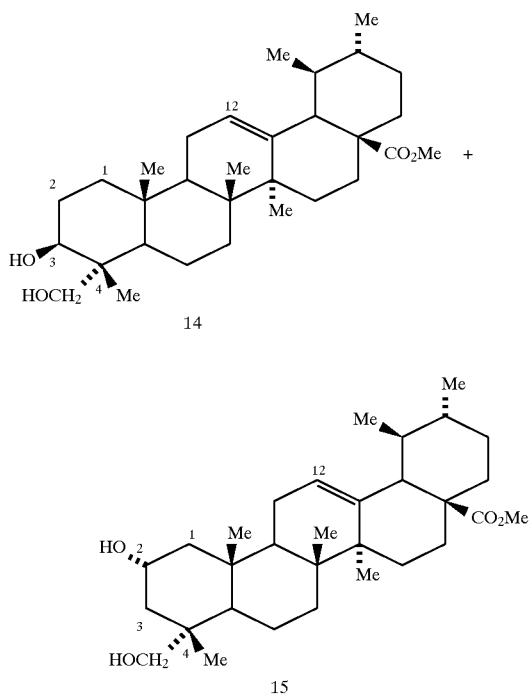

Process 8

Also, under the same reduction condition as described in said Scheme 7, reduction of the compound (13) is made and then followed by desilylation with tetrabutylammonium fluoride, thus further enhancing the ratio of compound (14) among the product [Scheme 8].

[Scheme 8]

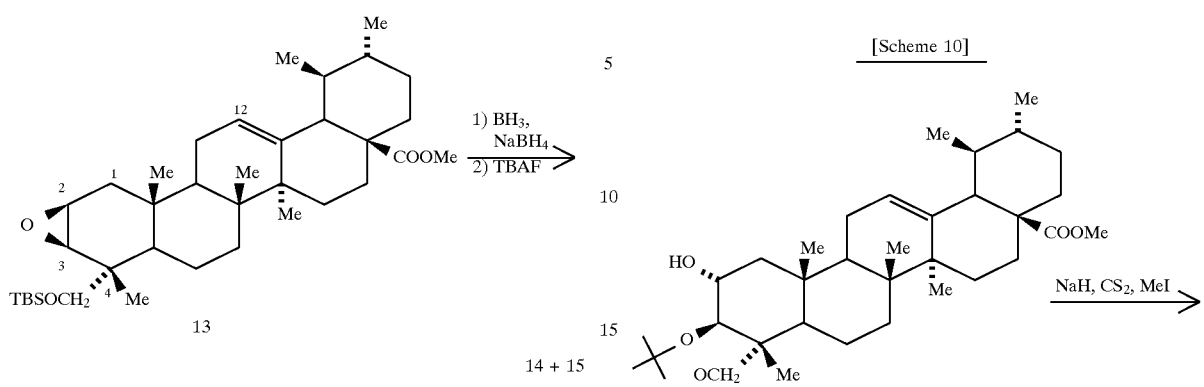

Process 9

Treatment of said prepared compound (14) with LAH may give of 2-deoxyasiatic alcohol (16) in high yield, one compound of the present invention [Scheme 9].

[Scheme 9]

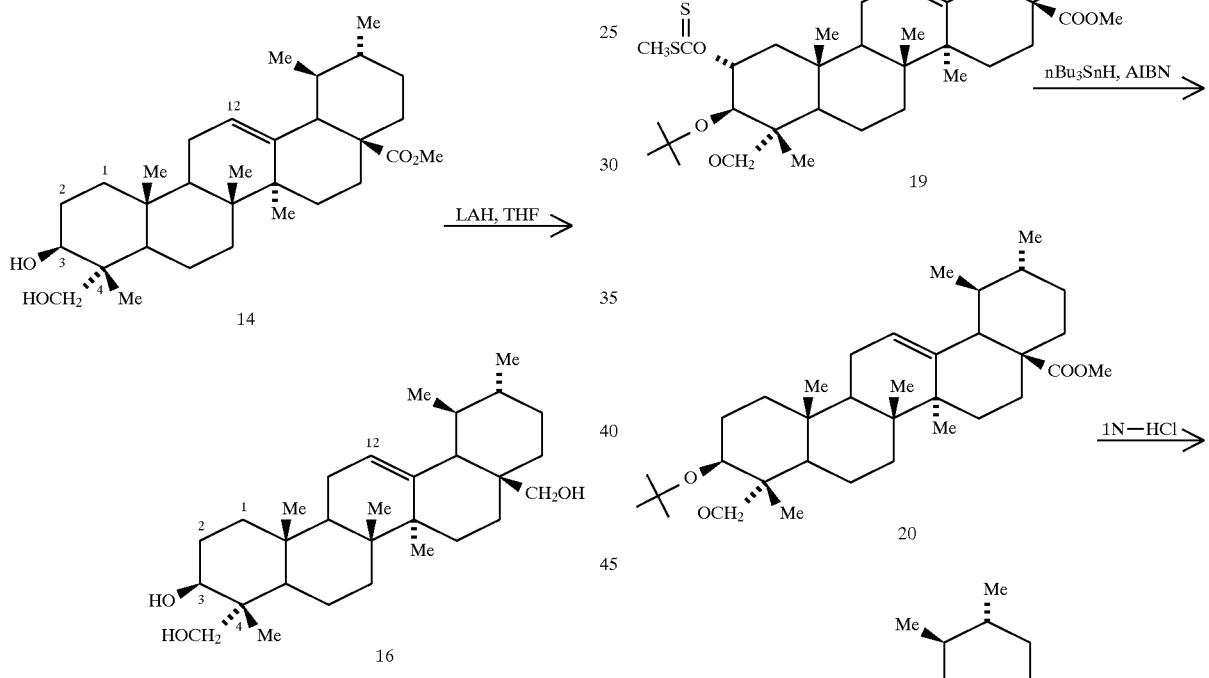

Process 10

The 2-OH position of methyl 3,23-O-isopropylidene asiatates (3) is treated with sodium hydride and imidazole for its conversion into alkoxide. Said compound is refluxed with the addition of carbon disulfide and then treated with methyl iodide to give xantate (19). Said xantate (19) is treated with tributyltin hydride and small amounts of AIBN to prepare methyl 2-deoxy-3,23-O-isopropylidene asiatate (20) and via the deprotecting reaction, methyl 2-deoxyasiatate (21) is prepared. Said compound (21) is hydrolyzed with lithium iodide in 2,4,6-collidine solvents to prepare 2-deoxyasiatic acid (22) [Scheme 10].

[Scheme 10]

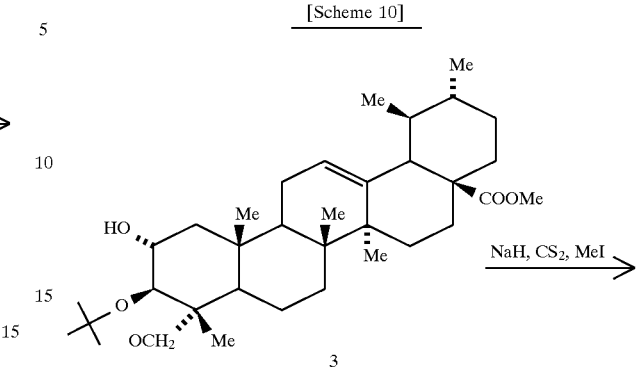

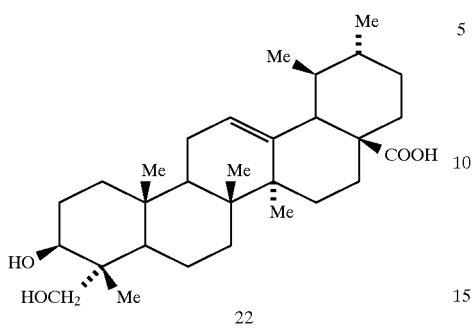

22

Process 11

The 2-hydroxy of methyl 3,23-O-isopropylidene asiatate (3) is protected with the benzyl and reduction of the ester sites with LAH produced 2-O-benzyl-3,23-O-isopropylidene asiaticol (24). Said compound (24) is mesylated with methanesulfonyl chloride and then substituted with sodium cyanide to prepare 2α-benzyloxy-28-cyano-3β,23-isopropylidenedioxyurs-12-ene (26). Said compound (26) is treated with hydrochloric acid/tetrahydrofuran to give 2α-benzyloxy-28-cyano-3β,23-dihydroxyurs-12-ene (27). Said compound (27) is treated with Pd/C to prepare 28-cyano-2,3,23-trihydroxyurs-12-ene(28) [Scheme 11].

[Scheme 11]

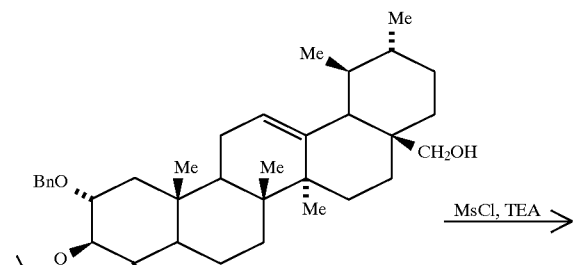

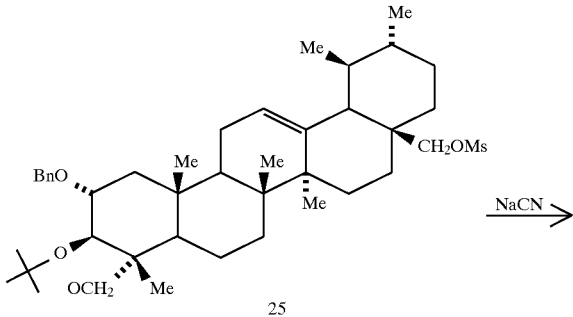

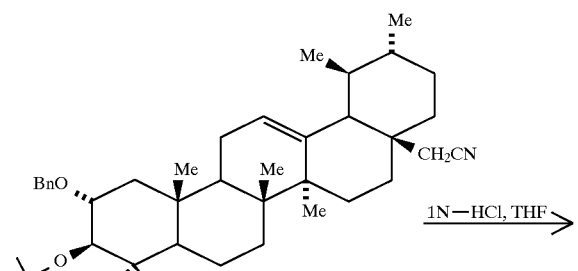

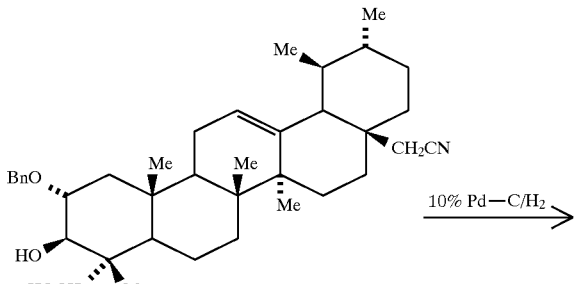

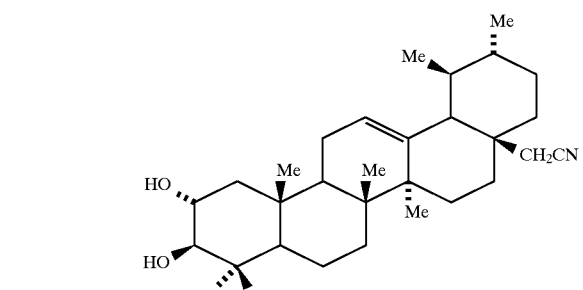

Process 12

By treating pyridinium dichromate (PDC) of the compound of the present invention (14=21), a compound (29), where the hydroxy at 3 position is oxidized with the oxo and hydroxymethyl at 4 position is converted to the methyl, is prepared. By reducing said compound (29) with sodium borohydride, the oxo at 3 position may be converted to the hydroxy. Further, by the Grignard reaction of the said compound, the alkyl or alkenyl may be introduced at 3 position (compound 31,32) [Scheme 12].

Process 13

By treating the compound of the present invention (4, R=methyl) with KHMDS and dimethylsulfate, the methoxy may be introduced at 2 position (compound 33). When this compound is treated with dilute hydrochloric acid and its protecting are removed, methyl 2-methoxyurs-12-ene-3-one-28-oate(34) is prepared [Scheme 13].

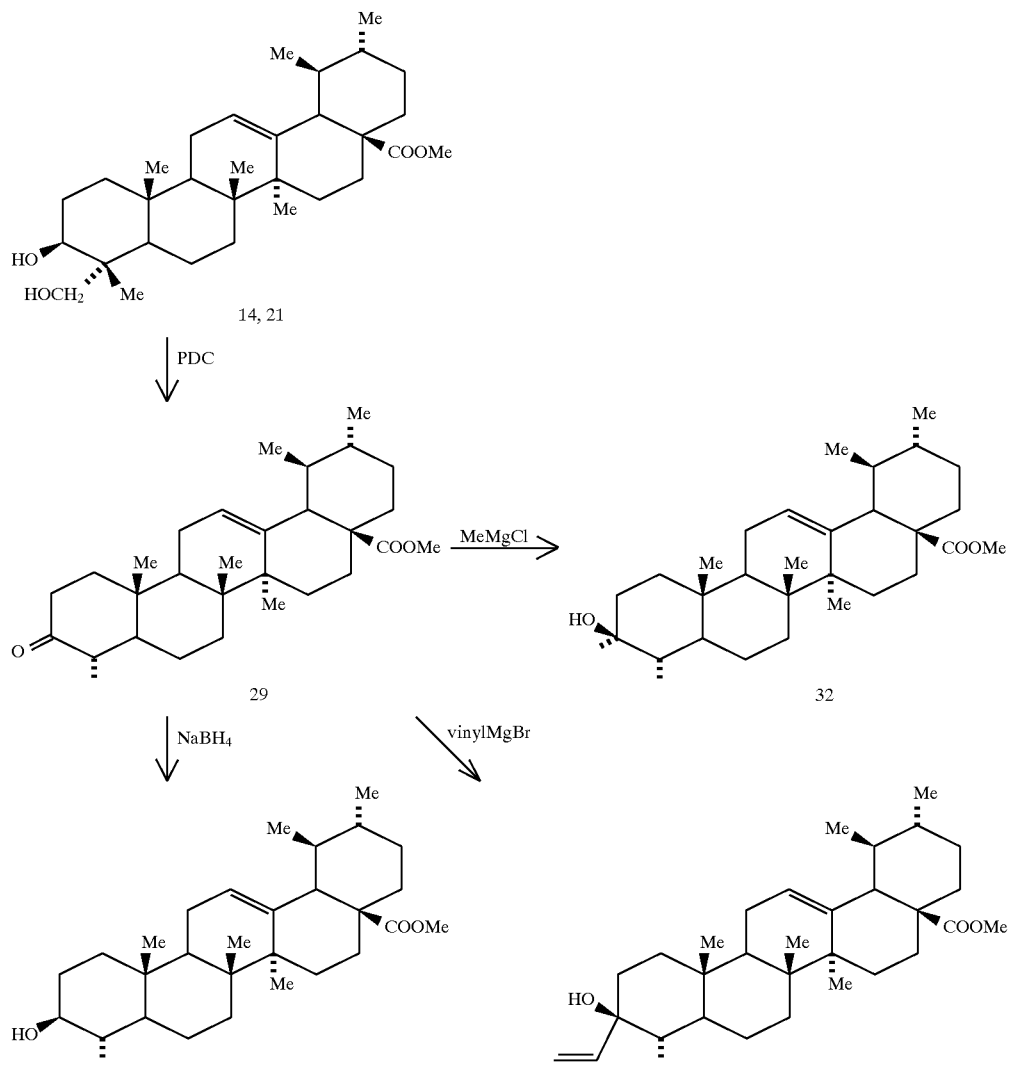

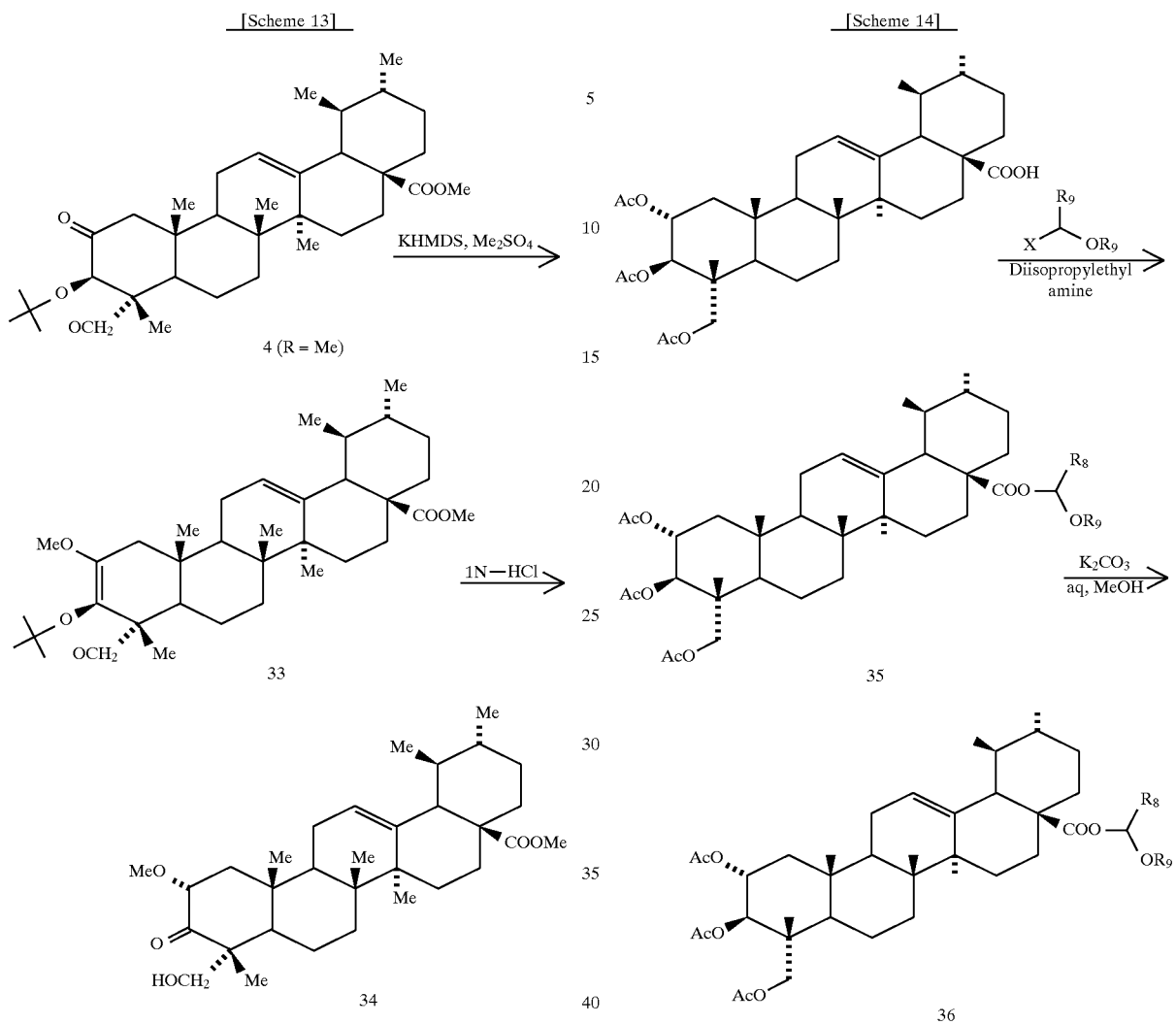

Process 14,15

Meantime, the corresponding esters (two compounds of the present invention (35, 37) are prepared by the following Schemes, [14] and [15]:

- After direct hydrolysis of *Centella asiatica* extracts, crude products are prepared via their neutralization and freeze-dried process. Triacetyl asiatic acid produced by direct acetylation of said crude products is reacted with alkoxymethyl chloride derivatives using base [Scheme 14], or
- Triacetyl asiatic acid is reacted with vinyl ether derivatives using catalytic amounts of acid [Scheme 15].

By treating said prepared triacetyl esters (35,37) with potassium carbonate/methanol, the selective deacetylation with presevation of ester sites in saccharide proceeded so that asiaticoside derivatives (36, 38) where a cyclic saccharide is combindned in ester linkage are prepared.

$R_8$ = H
$R_9$ = $CH_3$, $C_2H_5$, Octyl, Bn, $CH_3OCH_2$
X = Cl, Br, I, OMs, OTs

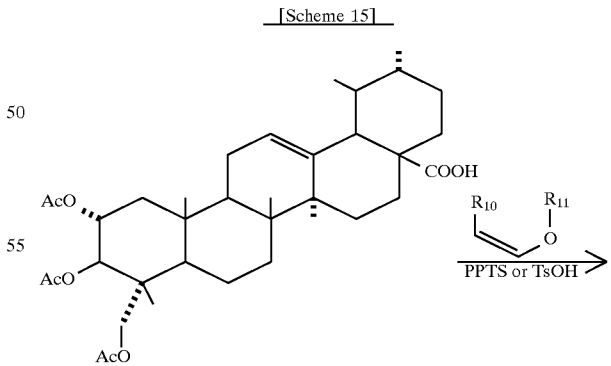

-continued
[Scheme 15]

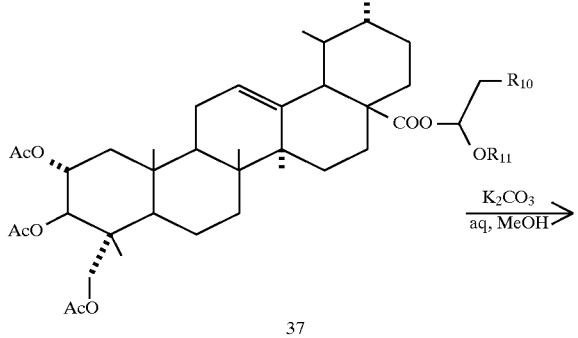

37

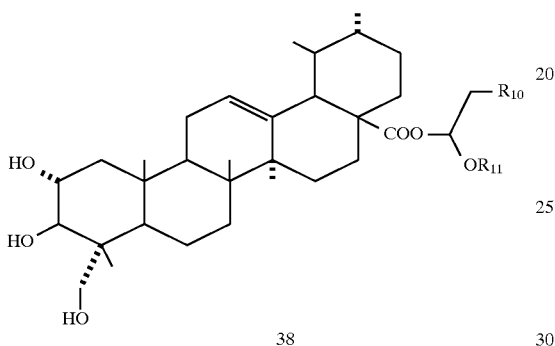

38

$R_{10} = H$
$R_{11} = C_2H_5, C_4H_9$
$R_{10} - R_{11} = -CH_2CH_2CH_2-, -CH_2CH_2-$

Process 16

Also, asiatic acid derivatives of the present invention contains their glycosides. In case of manufacturing said glycoside compounds, the selective and effective protection of hydroxy of saccharide is important. According to the present invention, the target glycosides could be prepared by protecting saccharide in acetylation, which has the following advantages: a) reaction may be easy, b) process is simple, c) high yield is expected, and d) deprotected reaction is also easy.

Scheme 16 shows that asiatic acid (or triacetyl asiatic acid), a starting material, is reacted with 2,3,4,6-tetra-O-acetyl-α-D-glucopyranosylbromide to prepare 2,3,4,6-tetra-O-acetyl-β-D-glucopyranosyl asiatate compound (39).

[Scheme 16]

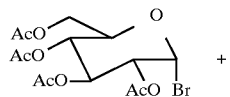

+

-continued
[Scheme 16]

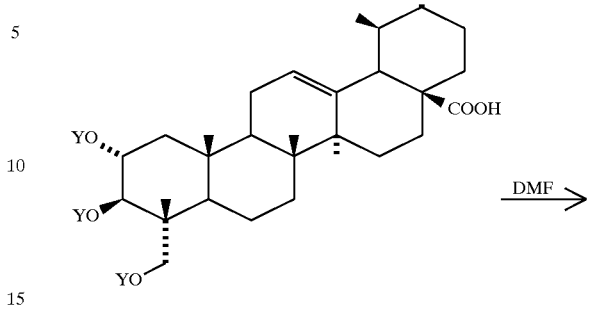

39

Y: H, Acetyl

In a similar process as above, α-L-rhamnose is acetylated to synthesize 1,2,3,4-tetra-O-acetyl-α-L-rhamnopyranose, followed by bromination with hydrobromic acid, to prepare 1,2,3,4-tetra-O-acetyl rhamnopyranosyl bromide. Then, said bromide is reacted with triacetyl asiatic acid to prepare tetraacetylrhamnopyranosyl triacetylasiatate (40).

From said prepared glycoside compounds (39, 40), acetyl combined with saccharides is easily hydrolyzed under extremely mild conditions. Accordingly, in case of using said glycoside compound as pharmaceuticals, it is conceivable that the acetyl in the body may be hydrolyzed into hydroxy. In case of said compounds (39,40) whose saccharide sites contain several acetyl, their lipophilicity becomes highly increasing and it is expected that their trandermal absorption may be further facilitated. And after transdermal absoption, their saccharide sites are hydrolyzed by skin esterase and this may facilitate the hydrolysis in ester sites, whereby asiatic acid may be easily freed in the body.

Process 17

Methyl 3,23-O-isopropylidene asiatate (3, R=methyl) is reacted with sodium hydride and alkyl iodide to alkylate the hydroxy at 2 position. By deprotecting acetonide with hydrochloric acid and methanol, methyl 2-O-alkylasiatate (41) is prepared. The hydroxy at 3, 23 positions of said compound is acetylated for protection and then oxidized with sodium dichromate using acetic acid to prepare methyl 3,23-O-diacetyl-2-O-alkyl-11-oxoasiatate (42) where the oxo at is introduced at 11 position.

Said compound is treated with potassium carbonate to deprotect the acetyl so that methyl 2-O-alkyl-11-oxoasiatate (43) is synthesized.

[Scheme 17]

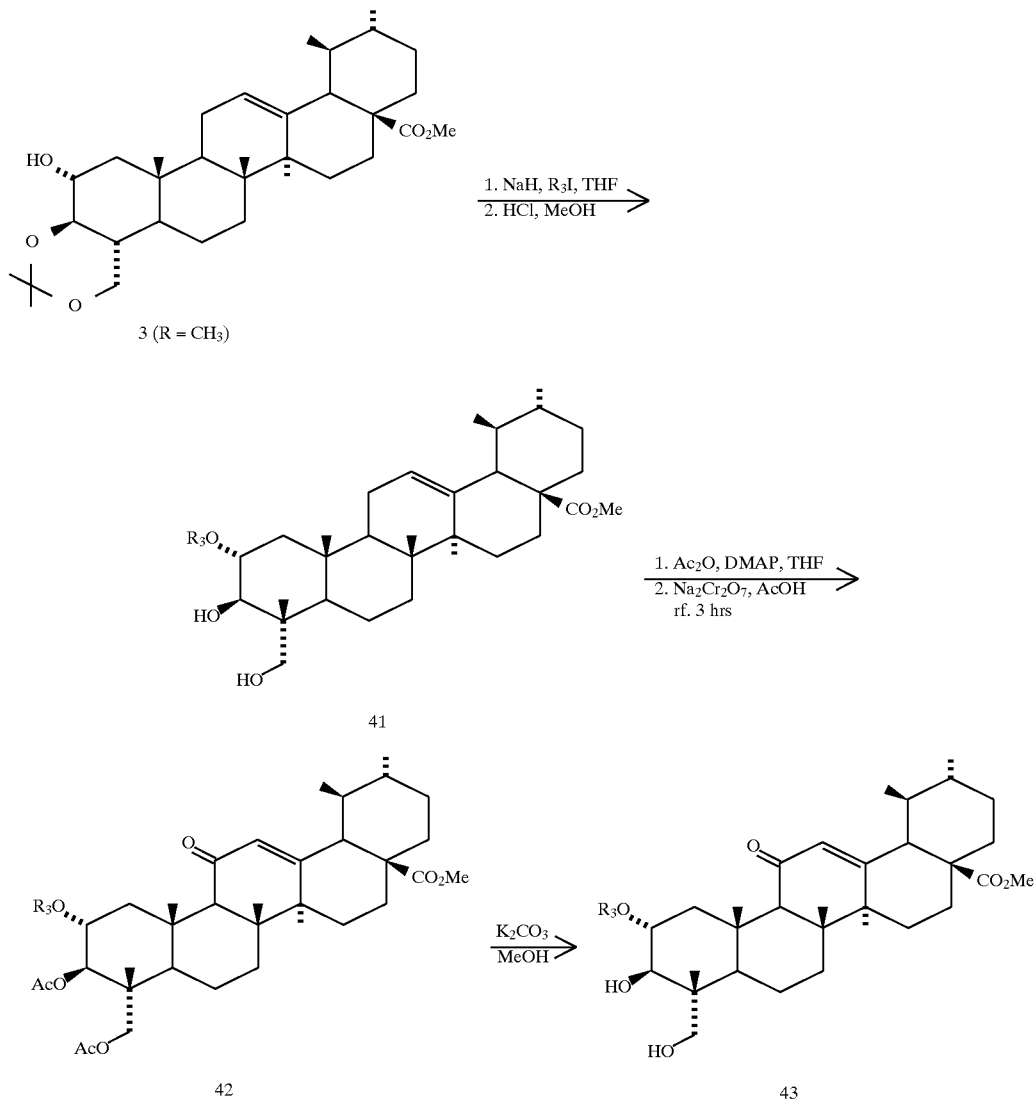

Process 18

The hydroxy at 2 position of methyl 3,23-O-isopropylidene asiatate (3, R=methyl) is acetylated with acetic anhydride for protection and then acetonide only is selectively deprotected with 0.1N HCl to synthesize methyl 2-O-acetylasiatate (44). Said compound (44) is oxidized with 1 anhydride for protection and then acetonide only is selectively deprotected with 0.1N HCl to synthesize methyl 2-O-acetylasiatate (44). Said compound (44) is oxidized with 1 equivalent of pyridinium dichromate at room temperature so that methyl 2-acetyloxy-3-hydroxyurs-12-ene-23-al-28-oate (45) is prepared. Said compound (45) is again oxidized by refluxing with 2 equivalent of pyridinium dichromate in dichloromethane to obtain methyl 2-acetyloxyurs-12-ene-23-al-3-one-28-oate (46).

[Scheme 18]
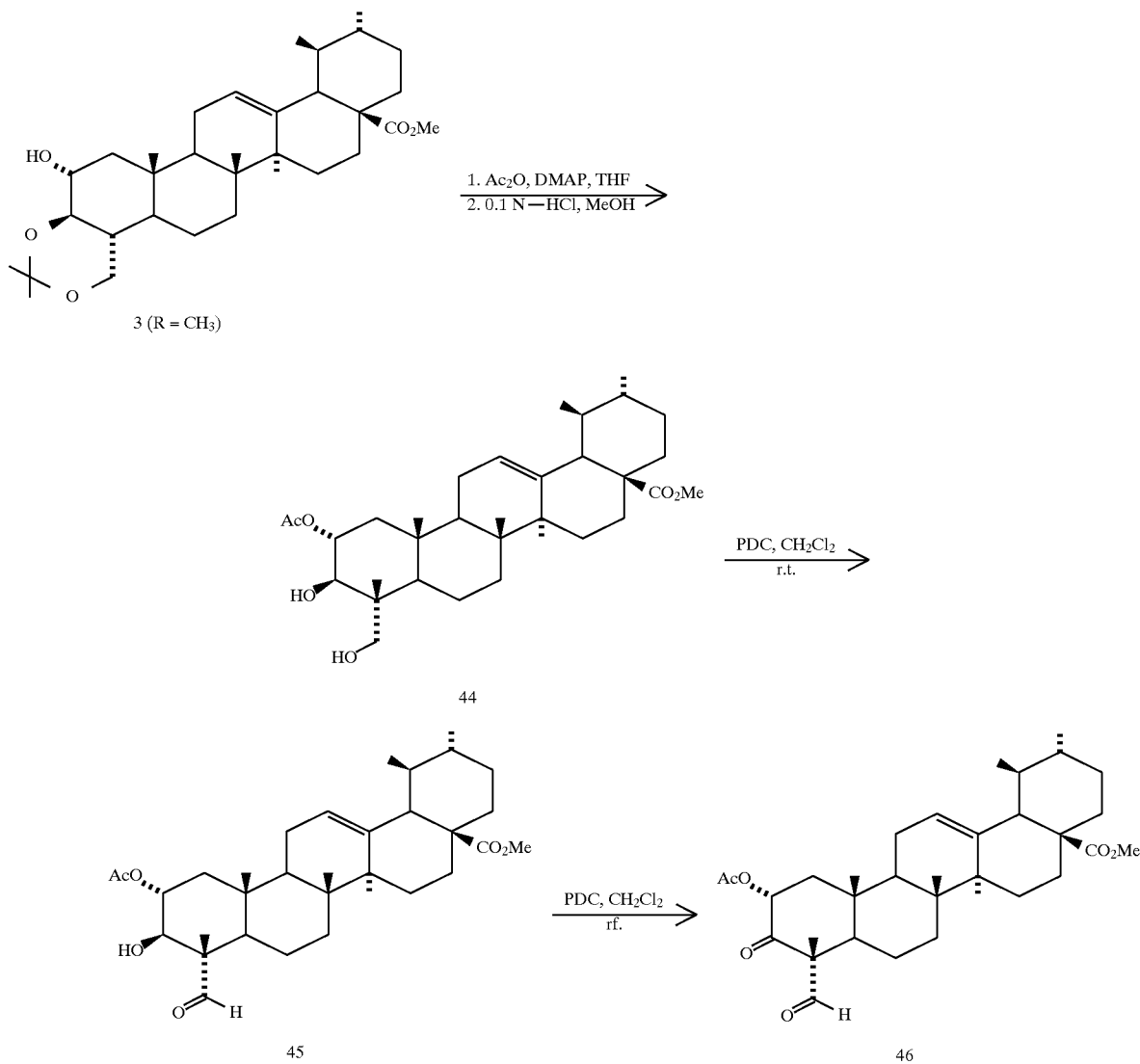
Process 19
As manufactured in said Process 11, methyl-2-O-benzyl-3,23-O-isopropylidene asiatate (23) is treated with hydrochloric acid for deprotecting acetonide only and then oxidized with pyridinium dichromate to synthesize methyl 2-O-benzyl-3-hydroxyurs-12-ene-23-al-28-oate (48).
[Scheme 19]
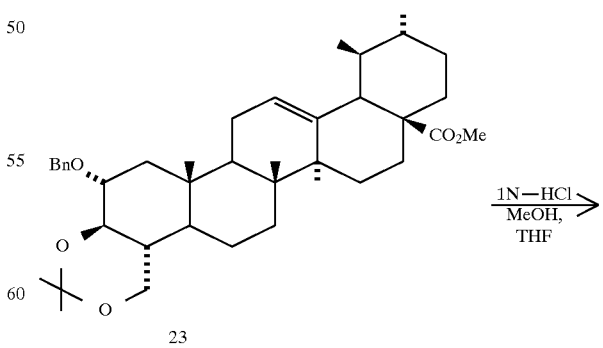

-continued
[Scheme 19]

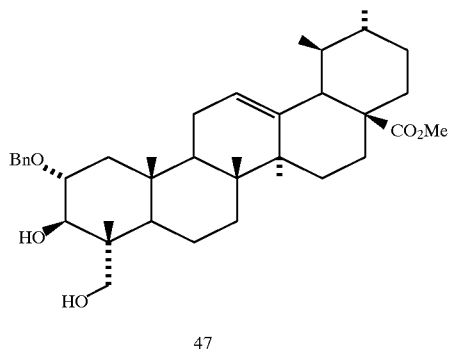

47

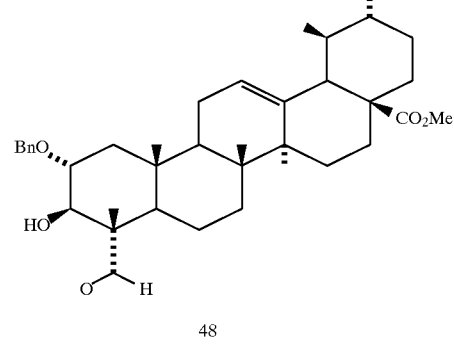

48

Process 20

As manufactured in said Process 11, 2-benzyloxy-28-cyano-3,23-dihyroxyurs-12-ene (27) is hydrolyzed with 80% potassium hydride to synthesize 2-benzyloxy-3,23-dihydroxyurs-12-ene-28-carboxylic acid (49). Said compound is contacted with Pd/C catalyst for reduction to prepare 2β, 3β, 23-trihydroxyurs-12-ene-28-carboxylic acid (homoasiatic acid).

[Scheme 20]

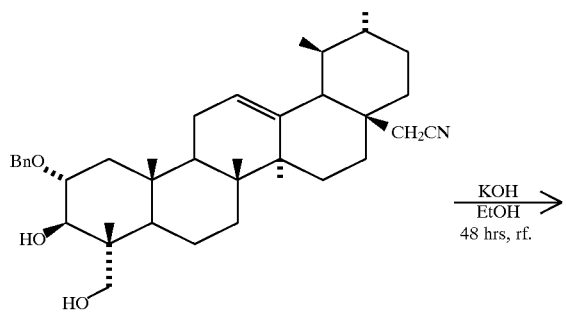

27

-continued
[Scheme 20]

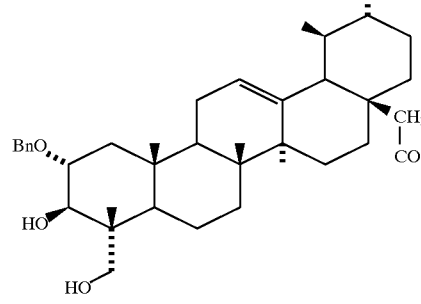

49

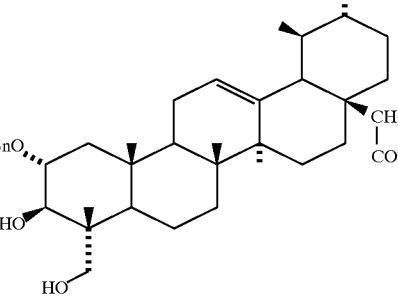

50

Process 21

3,23-O-isopropylidene-2-oxoasiatic acid (51) is reacted with chloromethylethyl ether using diisopropylethylamine as Hunig base to synthesize ethoxymethyl 3,23-isopropylidenedioxyurs-12-ene-2-one-28-oate (52). Under the same condition, said compound (51) is reacted with chloromethyloctyl ether to synthesize octyloxymethyl 3,23-isopropylidenedioxyurs-12-ene-2-one-28-oate (53).

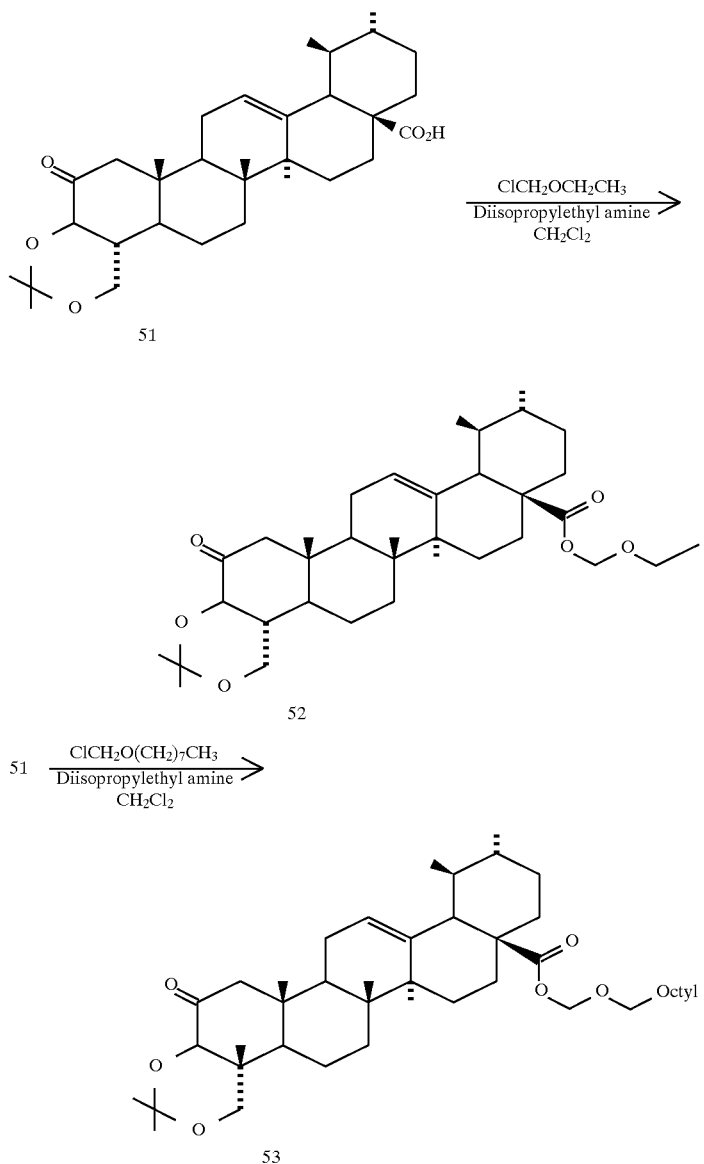

Process 22

The hydroxy at 2 position of 3,23-O-isopropylidne asiatic acid (3,R=H) is acetylated for protection. Then, compound (54) so obtained is reacted with chloromethyletyl ether and chloromethyloctyl ether, respectively, using diisopropylethylamine as Hunig base to synthesize both ethoxymethyl-2-α-acetyloxy-3β,23-isopropylidenedioxyurs-12-ene-28-oate (55) and octyloxymethyl 2-α-acetyloxy-3β,23-isopropylidenedioxyurs-12-ene-28-oate (56). Said prepared compounds (55), (56) are treated with potassium carbonate, respectively, for deprotecting acetyl, whereby ethoxymethyl 2α-hydroxy-3β, 23-isopropylidenedioxyurs-12-ene-28-oate (58) and octyloxymethyl 2α-hydroxy-3β, 23-isopropylidenedioxyurs-12-ene-28-oate (59) are synthesized.

2-acetyl-3,23-O-isopropylidene asiatic acid(54) is reacted with dihydropyran using pyridinium p-toluenesulfonate (PPTS) to synthesize 2-tetrahydropyranyl 3β, 23-isopropylidenedioxyurs-12-ene-28-oate (57).

[Scheme 22]
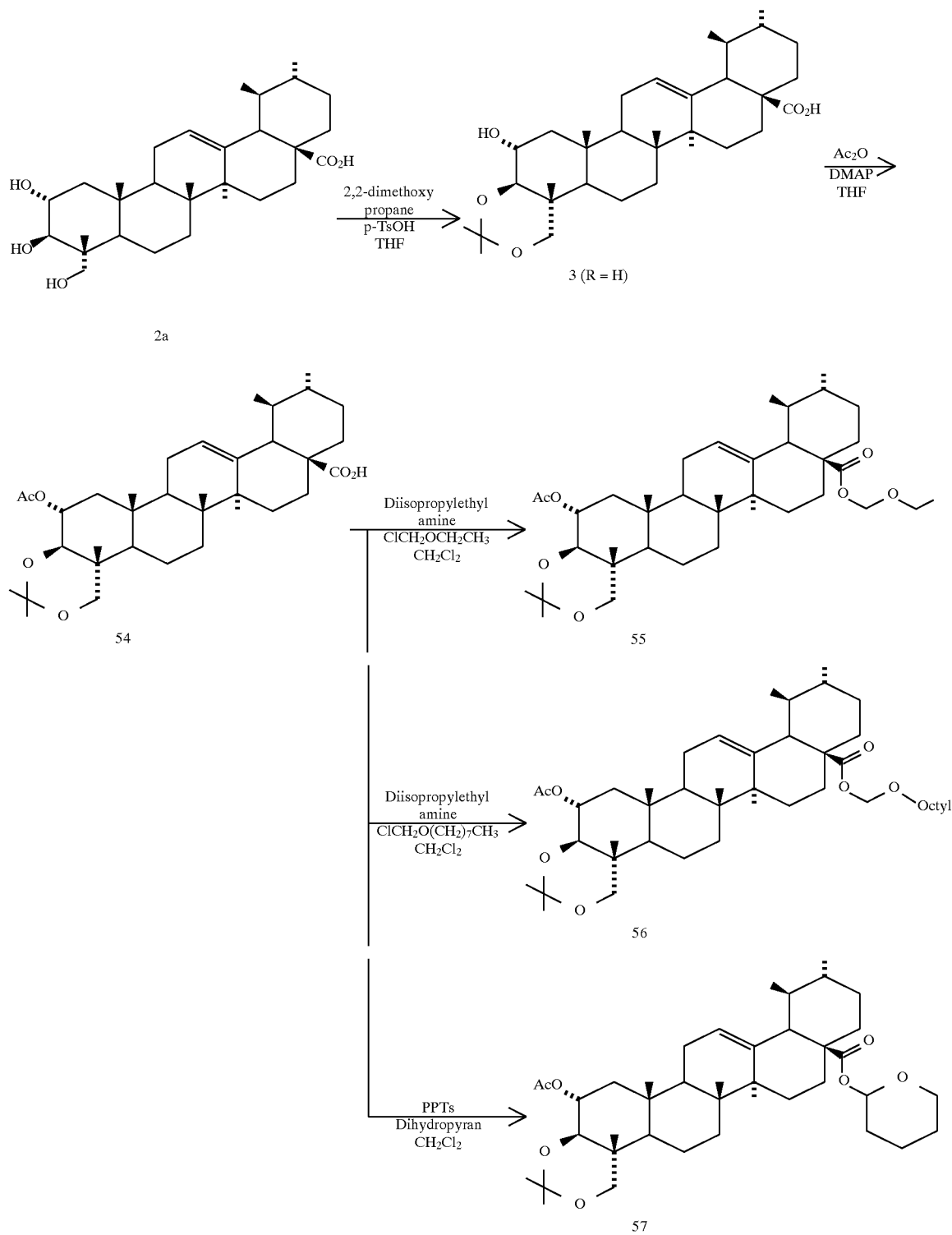

-continued
[Scheme 22]

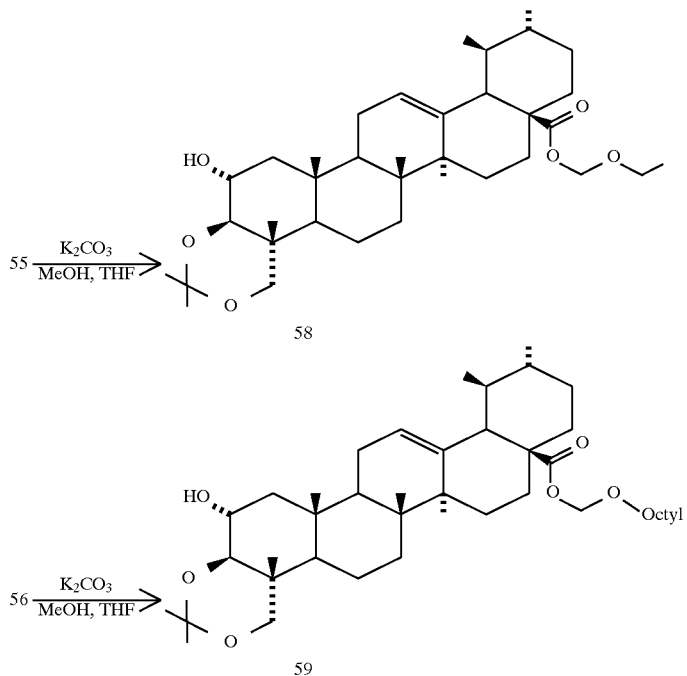

Process 23

The hydroxy s at 3, 23 positions of 2-deoxyasiatic acid (22) are acetylated for protection, to prepare 2-deoxy-3,23-diacetyl asiatic acid (60). Said compound (60) is reacted with dihydropyran using pyridinium p-toluenesulfonate to prepare 2-tetrahydropyranyl 3β, 23-diacetyloxyurs-12-ene-28-oate (61).

Said compound (60) is reacted with chloromethylethyl ether and chloromethyloctyl ether, respectively, using diisopropylethylamine to synthesize both ethoxymethyl 3β,23-diacetyloxyurs-12-ene-28-oate (62) and octyloxymethyl 3β, 23-diacetyloxyurs-12-ene-28-oate (63). Said prepared compounds(62), (63) are treated with potassium carbonate, respectively, and after hydrolyzing their acetyl, both ethoxymethyl 3β, 23-dihydroxyurs-12-ene-28-oate (64) and octyloxymethyl 3β, 23-dihydroxyurs-12-ene-28-oate (65) are prepared.

[Scheme 23]

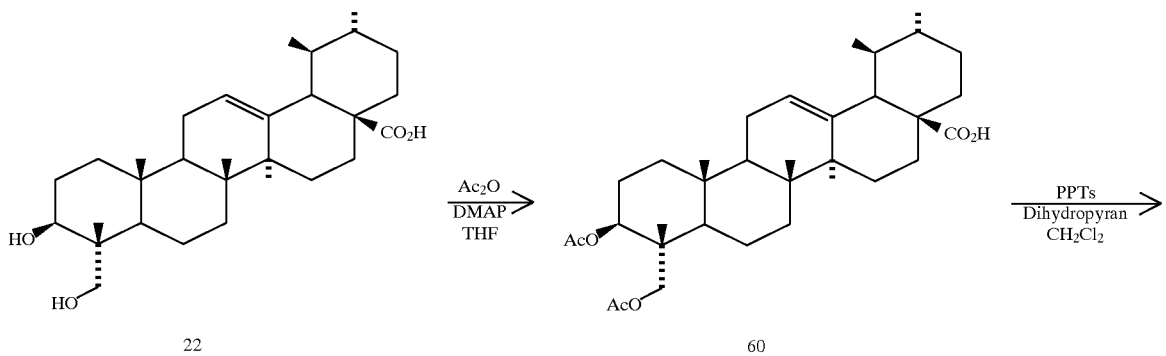

-continued
[Scheme 23]
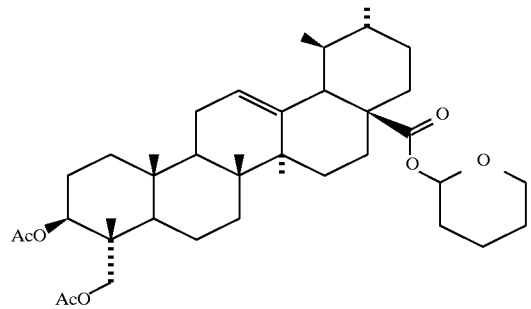
61
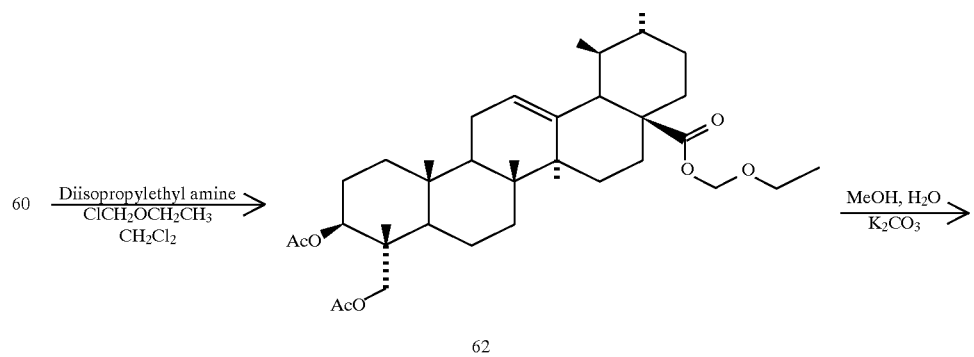
62
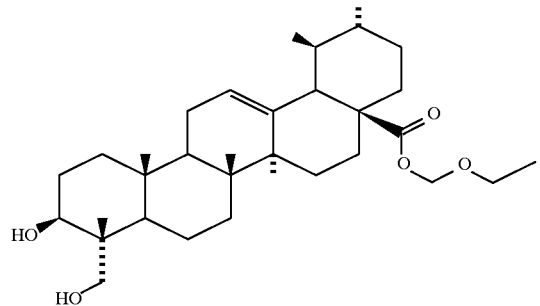
64
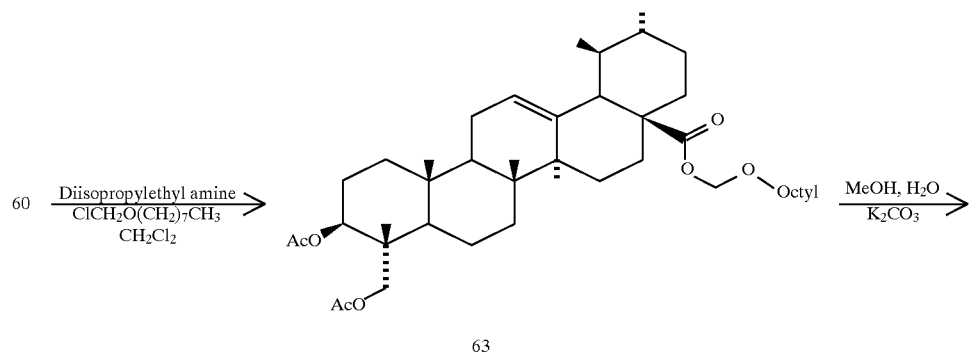
63

-continued
[Scheme 23]

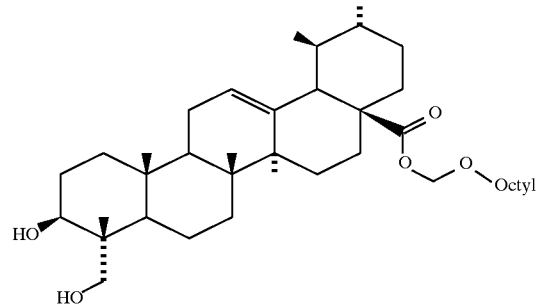

65

Process 24

Methyl 2β, 23-dihydroxyurs-12-ene-28-oate (66), together with lithium iodide, were heated for refluxed using 2,4,6-trimethylpyridine (collidine) and then hydrolyzed to synthesize 2β, 23-dihydroxyurs-12-ene-28-oic acid (67). The hydroxy at 2β, 23 positions of said prepared compound (67) were acetylated to prepare 2β, 23-diacetyloxyurs-12-ene-28-oic acid (68). Said compound (68) is reacted with dihydropyran using pyridinium p-toluenesulfonate as a catalyst to prepare 2-tetrahydropyranyl 2β, 23-diacetyloxyurs-12-ene-28-oate (71).

Said compound (68) is reacted with chloromethylethyl ether and chloromethyloctyl ether, respectively, using diisopropylethylamine, respectively, to synthesize both ethoxymethyl 2β, 23-diacetyloxyurs-12-ene-28-oate (69) and octyloxymetyl 2β, 23-diactyloxyurs-12-ene-28-oate (70). Said prepared compounds (69), (70) were deproteced with KOH, respectively, to synthesize both ethoxymethyl 2β, 23-dihydroxyurs-12-ene-28-oate(72) and octyloxymethyl 2β, 23-dihydroxyurs-12-ene-28-oate (73).

[Scheme 24]

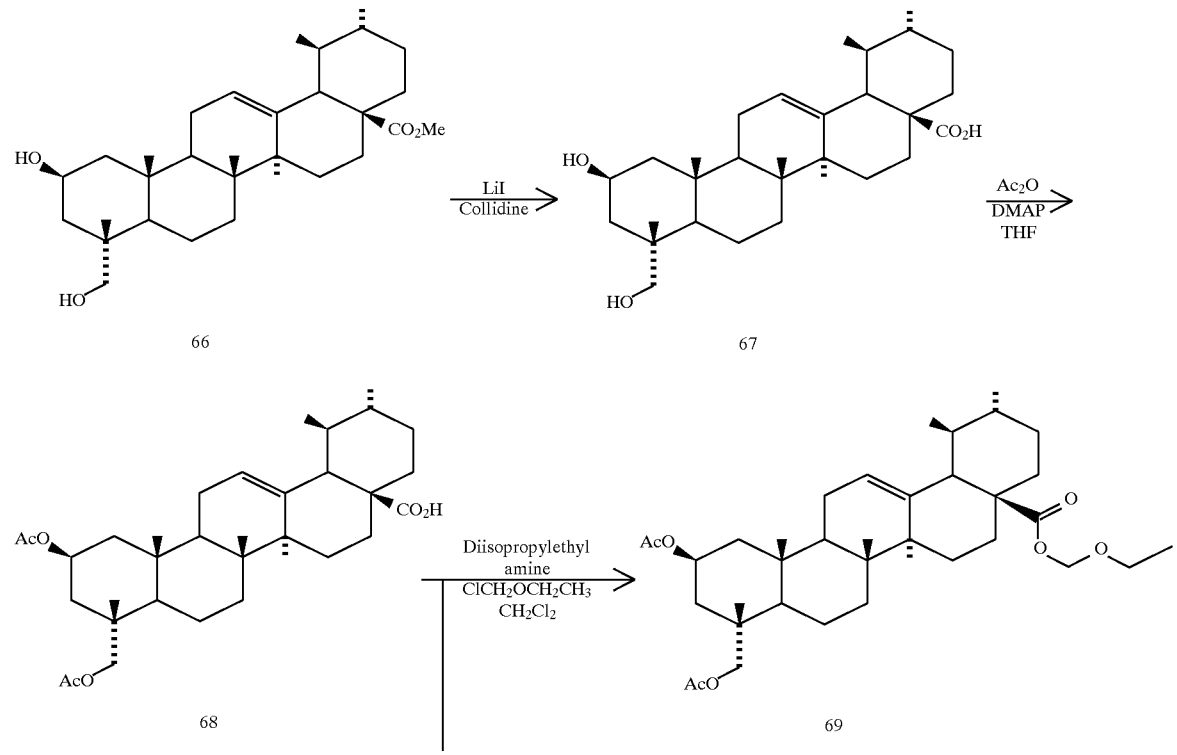

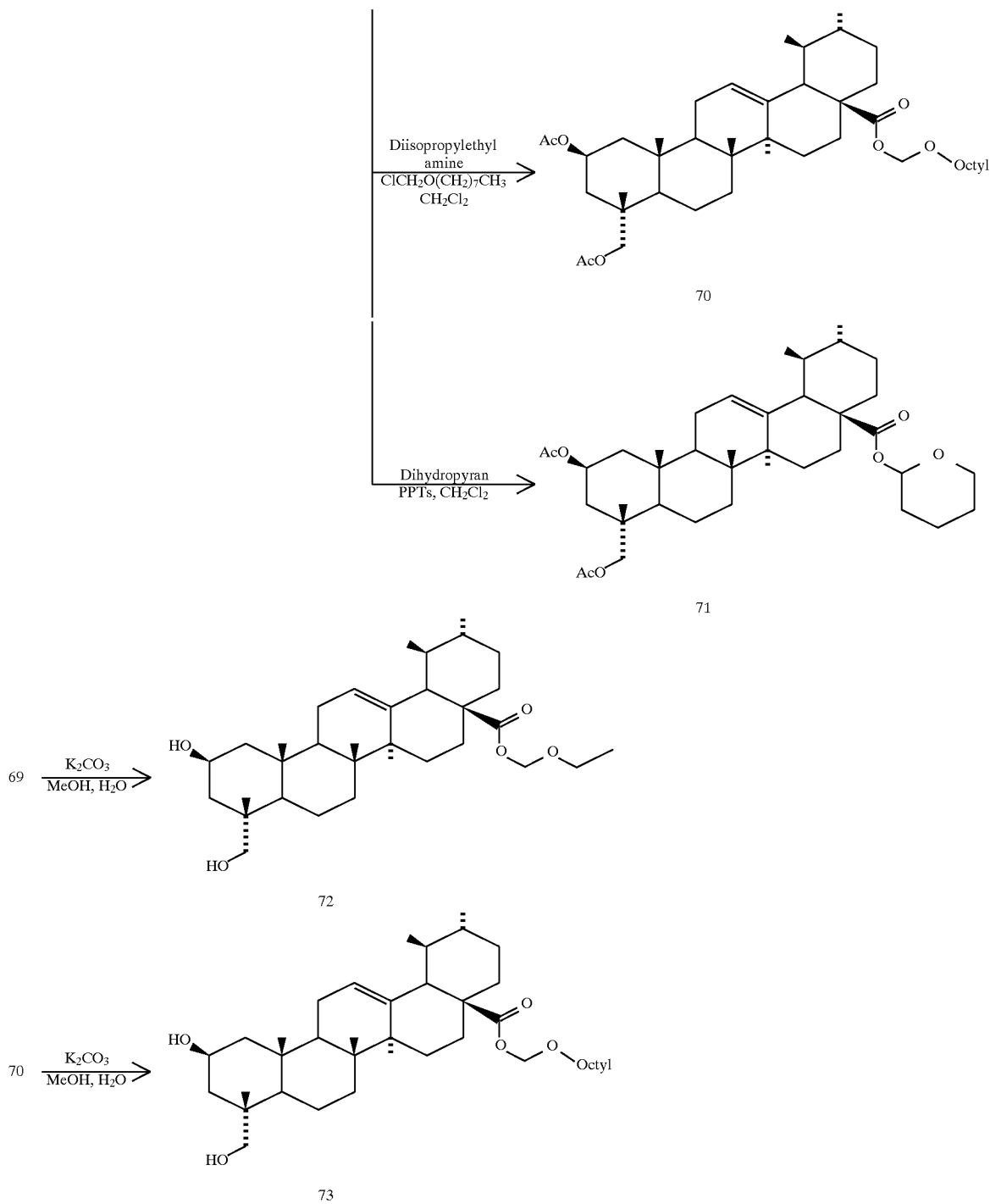
Process 25
Methyl 2β, 3β epoxy-23-hydroxyurs-12-ene-28-oate(10) synthesized from Process 4 is reacted with trimethylsilylazide or thiophenol as nuclophile using Ti(O—i—Pr)4, thus obtaining 2-azidoasiatic acid ester (74) and 2-thiopenoxyasiatic acid ester (75), respectively.
[Scheme 25]
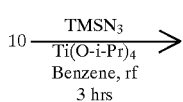

[Scheme 25] -continued

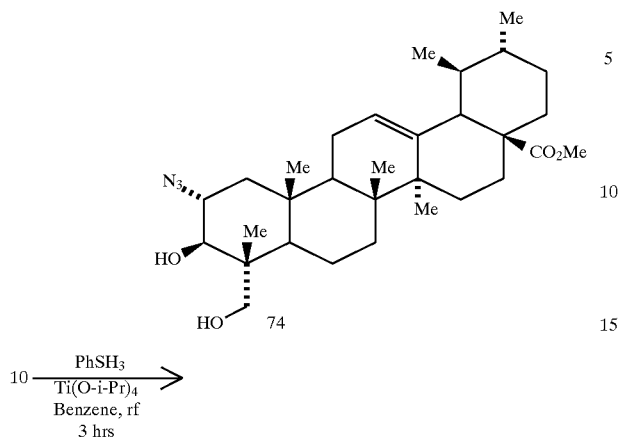

74

10 →[PhSH₃ / Ti(O-i-Pr)₄ / Benzene, rf / 3 hrs]→

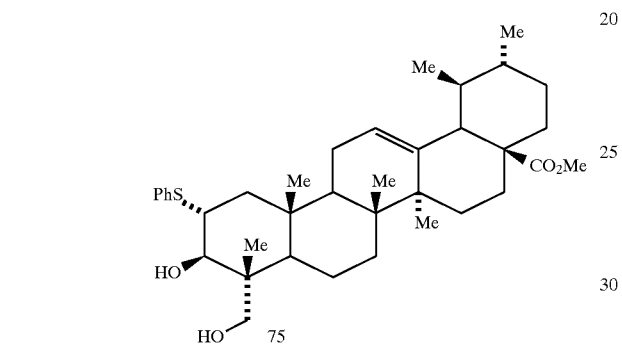

75

Process 26

To increase their lipophilicity of each hydroxymethyl related to 2-deoxyasiatic acid ester (14) prepared from Process 7 and methyl 2β, 3β-epoxy-hydroxyurs-12-ene-28-oate (10) prepared from Process 4, undecylenic acid is reacted to synthesize the corresponding esters (76) and (77), respectively.

[Scheme 26]

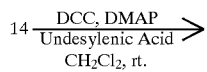

14 →[DCC, DMAP / Undesylenic Acid / CH₂Cl₂, rt.]→

[Scheme 26] -continued

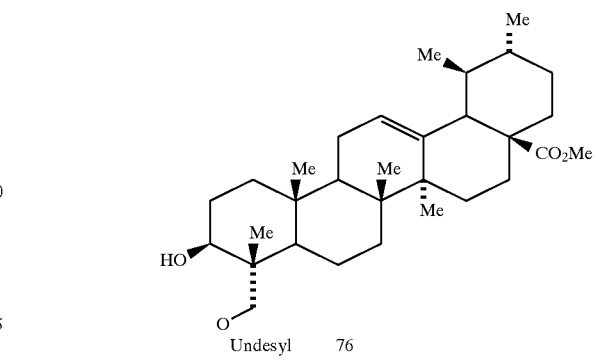

Undesyl 76

10 →[DCC, DMAP / Undesylenic Acid / CH₂Cl₂, rt.]→

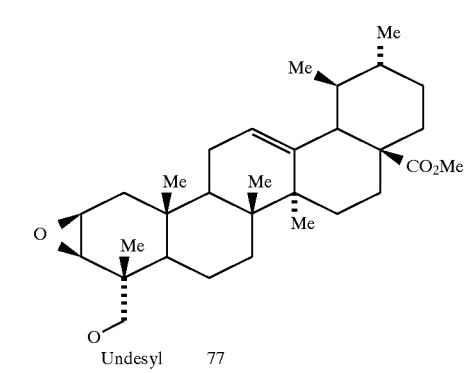

Undesyl 77

Process 27

The hydroxymethyl of methyl 2β, 3β-epoxy-23-hydroxyurs-12-ene-28-oate(10) of Process 4 is oxidized with Jones reagent to prepare epoxy acid (78). Said methyl 2β, 3β-epoxyurs-12-ene-28-oate-23 oic acid (78) is treated with diazomethane to synthesize epoxy ester or methyl 2β, 3β-epoxyurs-12-ene-23-(N-phenyl) amido-28-oate(80) by reacting said methyl 2β, 3β-epoxyurs-12-ene-28-oate-23-oic acid (78) with aniline.

[Scheme 27]

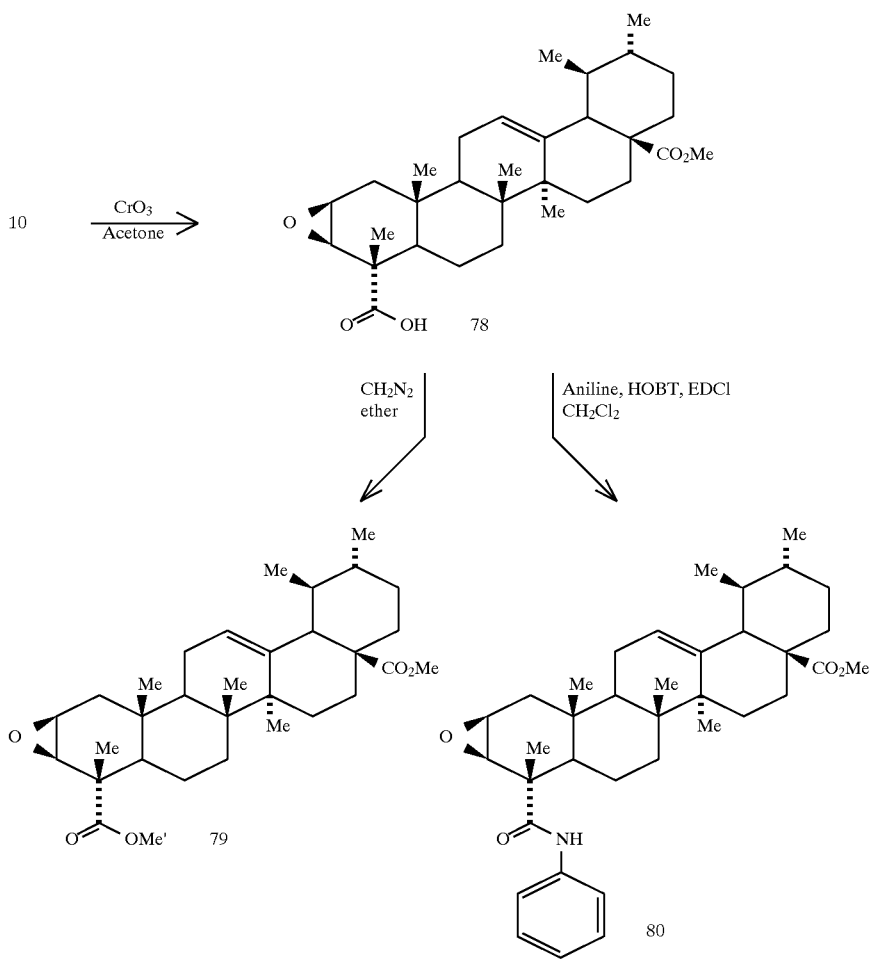

As a result of investigating the wound-healing property of asiatic acid derivatives of the present invention, when rats are given wounds, their efficacious are equivalent to 1% TECA (Titrated Extracted *Centella asiatica*), a control drugs or more remarkable.

The present invention is described in more detail by Examples and Experiments as shown below but is not confined to said scopes.

EXAMPLE 1

Separation and purification of asiaticoside and asiatic acid in mass-scale

An extract (5g) of *Centella asiatica* was directly separated on silica gel chromatography (silical gel, 230–400 mesh, dichloromethane:methanol=10:1) to give asiatic acid (1.5 g), madecassic acid (1.4 g) and a mixture (2.0 g) containing asiaticoside and madecasoside. The mixture, so obtained, was dissolved in catalytic amounts of 60% methanol on water bath at 100° C. and then cooled at room temperature to yield pure asiaticoside as needle crystal (mp.: 230°–240° C.). Aside from that, said extract (20 g) is dissolved in methanol (500 ml) and then hydrolyzed with 5N—NaOH. This is purified with column chromatography to give pure asiatic acid (7–8 g) as white solid (mp: 300°–310° C.).

TLC (methanol/dichloromethane=1:8) $R_f$ 0.32

EXAMPLE 2

Preparation of methyl 3,23-O-isopropylidene asiatate (3)

Methyl asiatate 2 (27.7 mg, 0.055 mmole) was dissolved in anhydrous acetone (3 ml), added with p-toluenesulfonic acid (27.7 mg) and then refluxed. Water was added to the reaction mixture, and the solution was neutralized with 5% potassium carbonate and then extracted with ethyl acetate. The organic layer was washed with water and brine, dried over anhydrous magnesium sulfate and then concentrated under reduced pressure. The was chromatographed with benzene and ethyl acetate (3:2) to give pure desired compound (18 mg, 60%).

$^1$H NMR (CDCl$_3$) δ 5.25(1H,m), 3.78(1H,m), 3.60(3H,s), 3.51(1H,d,J=10.5 Hz), 3.47(1H,d,J=10.5 Hz), 3.32(1H,d,J=9.5 Hz), 1.46(3H,s),1.45(3H,s), 1.09(3H,s) 1.07(3H,s), 1.04(3H,s), 0.94(3H,d,J=6.0 Hz), 0.86(3H,d,J=7.0 Hz), 0.73 (3H,s)

EXAMPLE 3

Preparation of methyl 3,23-O-isopropyliden-2-oxoasiatate (4, R=methyl)

Compound 3 (1.25 g, 2.31 mmole) was dissolved in dichloromethane (8 ml), added with pyridinium dichromate (0.61 g, 1.62 mmole) and acetic anhydride (0.71 g, 6.93 mmole) and then refluxed under nitrogen atmosphere. The reaction mixture was added with ethyl acetate (50 ml) and then filtered. The organic layer was washed with brine solution and dried over anhydrous magnesium sulfate. After filtration, the remaining solution was concentrated under reduced pressure. The was chromatographed with hexane and ethyl acetate (2:1) to give pure desired compound (1.107 g, 89%) as white solid.

$^1$H NMR (CDCl$_3$) δ 5.25(1H,m), 4.40(1H,s), 3.69(1H,d, J=10.5 Hz), 3.60(3H,s), 3.59(1H,d,J=10.5 Hz), 2.40(2H,d, J=12.5 Hz), 1.52(3H,s), 1.45(3H,s), 1.08(3H,s), 1.05(3H,s), 1.02(3H,s), 0.95(3H,d,J=6.0 Hz), 0.86(3H,d,J=6.5 Hz), 0.74 (3H,s)

3,23-O-isopropyliden-2-oxoasiatic acid (4, R—H)

$^1$H NMR (CDCl$_3$) δ 5.23(1H,m), 4.39(1H,bs), 3.62(1H, bs), 3.49(1H,bs), 2.62(1H,s), 1.50(3H,s), 1.44(3H,s), 1.24 (3H,s), 1.13(3H,s) 1.01(3H,s), 0.95–0.85(6H,m), 0.75(3H,s)

EXAMPLE 4

Preparation of methyl 2-oxoasiatate (5, R=methyl)

Compound 4 (R=methyl; 448.3 mg, 0.83 mmole) was dissolved in methanol (25 ml), added with p-toluenesulfonic acid (179.3 mg, 0.94 mmole) and then refluxed under nitrogen atmosphere. Water (500 ml) was added to the reaction mixture, and the solution was neutralized with 5% potassium carbonate and then extracted with ethyl acetate (50 ml×3). The organic layer was washed with brine, dried over anhydrous magnesium sulfate and then concentrated under reduced pressure. The residue was chromatographed with hexane and ethyl acetate (2:1) to yield pure desired compound (340 mg, 82%) as white solid.

$^1$H NMR (CDCl$_3$) δ 5.29(1H,m), 4.37(1H,m), 3.74(1H, m), 3.60(3H,s), 3.52(1H,m), 1.14(3H,s), 1.08(3H,s), 0.91 (9H,bs), 0.76(3H,s)

2-oxoasiatic acid (R=H)

$^1$H NMR (CDCl$_3$) 5.27(1H,m), 4.29(1H,s), 3.53–3.42 (2H,m), 1.13(3H,s), 1.02(3H,s), 0.96(3H,bs), 0.88(3H,S), 0.87(3H,d,J=7.0 Hz), 0.76(3H,d,J=3.8 Hz)

EXAMPLE 5

Preparation of methyl 2β-hydroxy-3β, 23-isopropylideneoxyurs-12-ene-28-oate (6)

Methyl 3,23-isopropyliden-2-oxoasiatate (4, R=H; 619.2 mg, 1.15 mmole) was dissolved in methanol (40 ml), added with sodium borohydride (21.9 mg, 0.58 mmole) and then stirred overnight under nitrogen atmosphere at room temperature. After completion of the reaction, the solvent was removed and the reaction mixture was extracted with ethyl acetate (50 ml×3). The organic layer was washed with water and brine solution, dried over anhydrous magnesium sulfate and then concentrated under reduced pressure. The residue was purified with column chromatography (hexane:ethyl acetate=2:1) to give pure desired compound (606.6 mg, 98%) as white solid.

$^1$H NMR (CDCl$_3$)δ

5.29(1H,m), 4.01(1H,bs), 3.59(3H,s), 3.49(3H,m), 1.44 (6H,bs), 1.31(6H,bs), 1.08(3H,s), 0.91(3H,d,J=4.0 Hz), 0.85 (3H,d,J=6.0 Hz), 0.75(3H,s)

EXAMPLE 6

Preparation of methyl 2β, 3β,23-trihydroxyurs-12-ene-28-oate (7, R=methyl)

Compound 6 (557.2 mg, 1.02 mmole), so obtained from said Example 5, was dissolved in methanol (15 ml), added with p-toluenesulfonic acid (223 mg, 1.17 mmole) and then refluxed under nitrogen atmosphere for 10 mins. Water (50 ml) was added to the reaction mixture, and the solution was neutralized with a solution of 5% potassium carbonate and then extracted with ethyl acetate (50 ml×3). The organic layer was washed with brine, dried over anhydrous magnesium sulfate and then concentrated under reduced pressure. The residue was purified with column chromatography (hexane:ethyl acetate=1:1) to give pure desired compound (407.3 mg, 79%) as white solid.

$^1$H NMR (CDCl$_3$) δ 5.26(1H,m), 4.11(1H,m), 3.75(1H, m), 3.72(1H,d,J=10.0 Hz), 3.60(3H,s), 3.42(1H,d,J=10.0 Hz), 1.30(3H,s), 1.11(3H,s), 1.06(3H,s), 0.94(3H,d,J=6.0 Hz), 0.85 (3H, d, J-6.0 Hz), 0.76 (3H, s)

2β, 3β, 23-trihydroxyurs-12-ene-28-oic acid (7, R=H)

$^1$H NMR (CDCl$_3$) δ 5.25(1H,m), 4.13(1H,m), 3.63(1H, J=4.1 Hz), 3.52(1H,d,J=10.9 Hz), 3.29(1H,d,J=10.9 Hz), 1.28(3H,s), 1.11(3H,s), 0.97(6H,s), 0.88(3H,d,J=6.5 Hz), 0.86(3H,d,J=4.1 Hz)

EXAMPLE 7

Preparation of methyl 2-methanesulfonyl-3,23-O-isopropylidene asiatate (8)

Methyl 3,23-O-isopropylidene asiatate 3 (354.7 mg, 0.65 mmole) was dissolved in dichloromethane (15 ml), added with triethyl amine (82.4 mg, 0.72 mmole) and methanesulfonyl chloride (99.2 mg, 0.98 mmole) and then stirred under nitrogen atmosphere at 0° C. for 3 hrs. After completion of the reaction, the solvent was removed and the reaction mixture was extracted with ethyl acetate (50 ml×3). The organic layer was washed with water and brine, dried over anhydrous magnesium sulfate and then concentrated under reduced pressure. The residue was purified with column chromatography (hexane:ethyl acetate=2:1) to give pure desired compound (380 mg, 93%) as white solid.

$^1$H NMR (CDCl$_3$) δ 5.24(1H,m), 4.69–4.62(1H,m), 3.60 (3H,s), 3.57(1H,d,J=10.5 Hz), 3.53(1H,d,J=10.5 HZ), 3.49 (1H,d,J=10.5 Hz) 3.01(3H,s), 2.26–2.20(1H,m),2.23(1H, bs), 1.44(3H,s), 1.40(3H,s), 1.11(3H,s), 1.09(3H,s), 1.07 (3H,s), 0.94(3H, d,J=6.0 Hz), 0.85(3H,d,J=7.0 Hz), 0.72 (3H,s)

EXAMPLE 8

Preparation of methyl 2-methanesulfonyl asiatate (9)

Compound 8 (1.2 g, 1.92 mmole) was dissolved in methanol (30 ml), added with p-toluensulfonic acid (480 mg, 2.52 mmole) and then refluxed under nitrogen atmosphere for 10 mins. Water (100 ml) was added to the reaction mixture, and the solution was neutralized with a solution of 5% potassium carbonate and then extracted with ethyl acetate (100 ml×3). The organic layer was washed with brine, dried over anhydrous magnesium sulfate and then concentrated under reduced pressure. The residue was purified with column chromatography (hexane:ethyl acetate=1:1) to give pure desired compound (1.06 g, 94%) as a colorless oil.

$^1$H NMR (CDCl$_3$) δ 5.24(1H,m), 4.77–4.74(1H,m), 3.69 (1H,d,J=10.5 Hz), 3.61(3H,s), 3.44(1H,d,J=10.5 Hz), 3.20 (1H,bs), 3.10(3H,s), 1.08(3H,s), 1.07(3H,s), 0.95(3H,s), 0.94(3H,d,J=5.1 Hz), 0.85(3H,d,J=6.5 Hz), 0.74(3H,s)

EXAMPLE 9

Preparation of methyl 2α, 3β-epoxy-23-hydroxyurs-12-ene-28-oate(10)

Compound 9 (2.78 g, 4.77 mmole) was dissolved in methanol (60 ml), added with potassium carbonate (1.32 g, 9.53 mmole) and then stirred under nitrogen atmosphere at room temperature for 3 days. After completion of the reaction, the solvent was removed and the reaction mixture was extracted with ethyl acetate (100 ml×3). The organic layer was washed with 5% dilute hydrochloric acid, water and brine, dried over anhydrous magnesium sulfate and then concentrated under reduced pressure. The residue was purified with column chromatography (hexane:ethyl acetate= 2:1) to give pure desired compound (2.05 g, 89%) as white solid.

$^{1}$H NMR (CDCl$_{3}$) δ 5.27(1H,m), 3.60(3H,s), 3.56(1H,m), 3.31(3H,m), 3.27(1H,m), 3.11(1H,d,J=4.0 Hz), 1.12(3H,s), 1.06(3H,s), 0.96 (3H,s), 0.94(3H,d,J=5.1 Hz), 0.86(3H,d,J= 6.4 Hz), 0.74(3H,s)

EXAMPLE 10

Preparation of 2α, 3β-epoxyurs-12-ene-23,28-diol (11) and 3-deoxyasiatic alcohol (12)

Compound 10 (140.9 mg, 0.29 mmole) was dissolved in tetrahydrofuran (5 ml) and added with lithium aluminum hydride (11.0 mg, 0.29 mmole). While agitating it under nitrogen atmosphere at room temperature, the reaction mixture was added with catalytic amounts of LAH until a starting material was entirely annihilated (about 2 days). The reaction was stopped by adding a mixture containing water and tetrahydrofuran (1:1) to the reaction mixture at 0° C. The reaction mixture was added with 5% dilute hydrochloric acid (10 ml) and extracted with ethyl acetate (50 ml×3). The organic layer was washed with a solution of saturated sodium carbonate, water and brine and dried over anhydrous magnesium sulfate and then concentrated under reduced pressure. The residue was purified with column chromatography (hexane:ethyl acetate=2:1) to give both pure compound 11 (44.1 mg, 33%) and 12 (63.3 mg, 47%) as white solid, respectively.

2α, 3β-epoxyurs-12-ene-23,28-diol (11)

$^{1}$H NMR (CDCl$_{3}$) δ 5.16(1H,m), 3.56–3.48(3H,m), 3.27 (1H,bs), 3.19(1H,d,J=10.3 Hz), 3.11(1H,d,J=4.0 Hz), 1.15 (3H,s), 1.09(3H,s), 0.99(3H,s), 0.98(3H,d,J=6.4 Hz), 0.93 (3H,s), 0.81(3H,d,J=5.6 Hz)

3-deoxyasiatic alcohol (12)

$^{1}$H NMR (CDCl$_{3}$) δ 5.08(1H,m), 4.04–3.97(1H,m), 3.47 (1H,d,J=11.0 Hz), 3.25(1H,d,J=11.0 Hz), 3.00(1H,d,10.9 Hz), 2.94(1H,d,J=11.0 Hz), 1.17(3H,s), 1.05(3H,s), 0.95 (3H,s), 0.84(6H,bs), 0.74(3H,d,J=5.9 Hz)

EXAMPLE 11

Preparation of 3-deoxyasiatic alcohol (12)

Compound 10 (87.4 mg, 0.18 mmole), so obtained from Example 9, was dissolved in tetrahydrofuran (5 ml), added with lithium aluminum hydride (13.6 mg,0.36 mmole) and then refluxed under nitrogen atmosphere for 1 hr. The reaction was stopped by adding a mixture containing water and tetrahydrofuran (1:1) in small portions to the reaction mixture at 0° C. The reaction mixture was added with 5% dilute hydrochloric acid (10 ml) and extracted with ethyl acetate (50 ml×3). The organic layer was washed with a solution of saturated sodium carbonate, water and brine and dried over anhydrous magnesium sulfate and then concentrated under reduced pressure. The residue was purified with column chromatography (hexane:ethyl acetate=2:1) to give pure desired compound (80.0 mg, 97%) as white solid.

EXAMPLE 12

Preparation of methyl 2-deoxy-23-tert-butyldimethylsilyl asiatate (13)

Compound 10 (200 mg, 0.41 mmole), so obtained from Example 9, was dissolved in dimethylform amid (5 ml), added with tert-butyldimethylsilyl chloride (68.5 mg, 0.45 nmole) and imidazole (61.9 mg, 0.91 mmole) and then stirred under nitrogen atmosphere at room temperature for 1 day. The reaction was stopped by adding a solution of saturated ammonium chloride to the reaction mixture at 0° C. and the reaction mixture was extracted with ethyl acetate (50 ml×3). The organic layer was washed with 5% dilute hydrochloric acid, a solution of saturated sodium carbonate, water and brine and dried over anhydrous magnesium sulfate and then concentrated under reduced pressure. The residue was purified with column chromatography (hexane:ethyl acetate=4:1) to yield pure desired compound (273.5 mg, >100%) as colorless oil.

$^{1}$H NMR (CDCl$_{3}$) δ 5.28–5.26(1H,m), 3.60(3H,s), 3.49 (1H,d,J=9.7 Hz), 3.32(1H,d,J=9.6 Hz), 3.21(1H,m), 3.04 (1H,d,J=4.1 Hz), 1.10(3H,s), 1.05(3H,s), 0.95(3H,s), 0.92–0.85(15H,m), 0.74(3H,s),0.05(3H,s), 0.04(3H,s).

EXAMPLE 13

Preparation of methyl 2-deoxyasiatate (14) and methyl 3-deoxyasiatate (15)

Compound 10 (77.5 mg, 0.16 mmolee), so obtained from Example 9, was dissolved in tetrahydrofuran (2 ml), added with dimethylsulfide (0.11 ml, 2M solution) and sodium borohydride (1.6 mg, 0.04 mmole) and then refluxed under nitrogen atmosphere for 1 day. The reaction was stopped by adding a mixture (1 ml) containing 1.0M sulfuric acid and tetrahydrofuran (1:1) at 0° C. to the reaction mixture, and the reaction mixture was extracted with ethyl acetate (50 ml×3). The organic layer was washed with a solution of saturated sodium carbonate, water and brine and dried over anhydrous magnesium sulfate and then concentrated under reduced pressure. The residue was purified with column chromatography (hexane:ethyl acetate=2:1) to give both pure compound 14 (48.4 mg, 62%) and pure compound 15 (16.3 mg, 21%) as white solid, respectively.

Methyl 2-deoxyasiatate (14)

mp.: 250°–254° C. $^{1}$H NMR (CDCl$_{3}$) δ 5.22(1H,m), 3.69(1H,d,J=10.3 Hz), 3.61–3.59(1H,m), 3.58(3H,s), 3.39 (1H,d,J=10.3 Hz), 2.18(1H,d,J=11.5 Hz), 1.05(3H,s), 0.94 (3H,s), 0.91(3H,d,J=5.0 Hz), 0.86(3H,s), 0.83(3H,d,J=6.5 Hz), 0.72(3H,s).

Methyl 2β, 23-dihydroxyurs-12-ene-28-oate (15)

$^{1}$H NMR (CDCl$_{3}$) δ 5.28(1H,m), 4.22–4.16(1H,m), 3.61 (3H,s), 3.42(1H,d,J=10.8 Hz), 3.18(1H,d,J=10.8 Hz), 1.24 (3H,s), 1.08(3H,s), 0.98(3H,s), 0.94(3H,d,J=5.5 Hz), 0.86 (3H,d,J=6.5 Hz), 0.77(3H,s).

EXAMPLE 14

Preparation of 2-deoxyasiatic alcohol (16)

Compound 14 (463 mg, 0.94 mmole) was dissolved in tetrahydrofuran (15 ml), added with lithium aluminum hydride (71.7 mg, 1.89 mmole) and then refluxed under nitrogen atmosphere for 3 hrs. The reaction was stopped by adding a mixture containing water and tetrahydrofuran (1:1) in small portions at 0° C. to the reaction mixture, followed by addition with 5% dilute hydrochloric acid (20 ml) and extraction with ethyl acetate (50 ml×3). The organic layer was washed with a solution of saturated sodium carbonate, water and brine and dried over anhydrous magnesium sulfate and then concentrated under reduced pressure. The residue was purified with column chromatography (hexane:ethyl acetate=1:1) to give pure desired compound (415.7 mg, 95%) as white solid.

¹H NMR (CDCl₃) δ 5.13(1H,m), 3.69(1H,d,J=10.3 Hz), 3.63(1H,m), 3.53(1H, d,J=10.9 Hz), 3.40(1H,d,J=10.3 Hz), 3.16(1H,d,J=10.8 Hz), 1.10(3H,s), 0.99(6H,s), 0.93(3H,s), 0.88(3H,s), 0.81(3H,bs).

EXAMPLE 15

Preparation of 3, 23-O-isopropyliden-2α-methylasiatic acid (17, R'=methyl)

3,23-O-isopropyliden-2-oxoasiatic acid (4, R=H; 1000 mg, 1.90 mmole) was dissolved in tetrahydrofuran (40 ml), and cooled to −78° C. Methylmagnesium chloride (3.0M THF Solution 1.9 ml, 5.60 mmole) was added to the mixture and stirred for 10 mins. The reaction mixture was treated with water (1 ml) and concentrated under reduced pressure to remove the solvent. The residue was added with ethyl acetate (50 ml) and a solution of saturated ammonium chloride (5 ml) and extracted. The organic layer was washed with brine solution (5 ml), dried over anhydrous magnesium sulfate and then concentrated under reduced pressure. The residue was purified with column chromatography (dichloromethane:methanol=50:1) to give pure desired compound (980 mg, 95%) as white solid.

$[\alpha]^{22}_D$;+53.4(CHCl₃,C=1.19) IR(neat):3400,1696 cm⁻¹ ¹H NMR (CDCl₃) δ 5.19(1H,bt), 3.37, 3.43(2H,d), 3.20(1H, s), 2.13(1H,d,J=9.2 Hz), 0.89(3H,d,J=6.0 Hz), 0.80(3H,d,J=6.4 Hz), 0.72, 1.03, 1.08, 1.21, 1.23, 1.36, 1.40, (each 3H,s).

EXAMPLE 16

Preparation of 3,23-O-isopropyliden-2α-ethylasiatic acid (17, R'=ethyl)

By the same procedure as described above for the preparation of Example 15, using ethylmagnesium bromide (1.0M THF Solution, 373 mg, 2.80 mmole) instead of methylmagnesium chloride, pure desired compound (490 mg, 92%) was obtained as white solid.

¹H NMR (CDCl₃) δ 5.26(1H,bt), 3.42, 3.51(2H,d,J=10.8 Hz), 3.28(1H,s), 2.18(1H,d), 1.41, 1.44(each 3H,s)

EXAMPLE 17

Preparation of 2α-methylasiatic acid (18, R'=methyl)

3,23-O-isopropyliden-2α-methylasiatic acid (17, R'=methyl; 370 mg, 0.68 mmole) was added with methanol (10 ml) and 1N hydrochloric acid (0.5 ml) and stirred at room temperature for 10 hrs. The reaction mixture was distilled under reduced pressure to remove the solvent. The residue was purified with column chromatography (dichloromethane:methanol=30:1) to give pure desired compound (325 mg, 95%) as white solid. The crude product was recrystallized from methanol to give needle crystal.

¹H NMR (CDCl₃) δ 5.15(1H,brt), 3.35(1H,s), 3.58(2H, AB q,J=10.4 Hz), 3.25, 2.15(1H,d,J=11.2 Hz), 0.79(3H,d, J=6.4 Hz), 0.73(3H,d, J=6.0 Hz), 1.18, 1.13, 0.93, 0.92, 0.66(3H, each s)

EXAMPLE 18

Preparation of 2α-ethylasiatic acid (18, R'=ethyl)

By the same procedure as described above for the preparation of Example 17, compound (17, R'=ethyl; 260 mg, 0.47 mmole) was deprotected to give white solid (227 mg, 94%). The residue was recrystallized from methanol to give needle crystal.

¹H NMR (CDCl₃) δ 5.32(1H,brt,J=3.4, 7.7 Hz), 3.53(1H, s), 3.75, 3.42(2H,AB q, J=10.3 Hz), 2.32(1H,d,J=11.7 Hz), 1.29, 1.12, 1.10, 0.86(each 3H,s)

EXAMPLE 19

Preparation of methyl 3,23-O-isopropyliden-2-O-[(methylthio) thiocarbonyl] asiatate Methyl 3,23-O-isopropylidene asiatate 3 (50 mg, 0.092 mmole) was added with sodium hydride (60% dispersion in mineral oil; 18.3 mg, 0.46 mmole), imidazole (2 mg) and tetrahydrofuran (2 ml), and the mixture was stirred for 30 mins. Then, carbon disulfide (0.2 ml, excess) was added to the mixture and refluxed for 2 hrs. Methyl iodide (0.1 ml, excess) and the mixture was heated for reflux for further 1 hr. The reaction mixture was treated with water (1 ml) and the solvent was distilled and removed under reduced pressure. The mixture was extracted with ethyl acetate (10 ml), washed with water (2 ml×3) and brine (2 ml×3) and then dried over anhydrous magnesium sulfate. The organic layer was concentrated under reduced pressure. The residue was purified with column chromatography (hexane:ethyl acetate=10:1) to give white solid (56 mg, 96%).

$[\alpha]^{25}_D$;−32.3(c=1.33,CHCl₃) IR(neat):1723, 1233, 1057 cm⁻¹ ¹H NMR (CDCl₃) δ 5.78(1H,m), 5.24(1H,bt), 3.80(1H, d,J=10 Hz), 3.60(3H,s)r 3.54, 3.58(2H,dd,J=7.2 Hz), 2.51 (3H,s) 2.23(1H,d,J=11.2 Hz), 0.94(3H,d,J=5.2 Hz), 0.84 (3H,d,J=6 Hz), 0.73, 1.09, 1.11, 1.14, 1.41, 1.45 (each 3H,s).

EXAMPLE 20

Preparation of methyl 2-deoxy-3,23-O-isopropylidene asiatate(20)

Xantate compound 19 (202 mg, 0.32 mmole) was added with catalytic amounts of AIBN and benzene (10 ml) and heated for reflux. The mixture was then added with tributyltin hydride (0.26 ml, 0.96 mmole) and stirred for 1.5 hrs. The reaction mixture was concentrated under reduced pressure to remove the solvent. The residue was purified with column chromatography (hexane:ethyl acetate=10:1) to give white solid (168 mg, 100%). The crude product was recrystallized from hexane to give needle crystal.

$[\alpha]^{25}_D$;+56.2 (c=1.07, CHCl₃) IR(neat):1724cm⁻¹ MS (EI):527(M⁺+1), 512, 407, 262, 203, 133. ¹H NMR (CDCl₃) δ 5.25(1H,bt), 3.60(3H,s), 3.52(1H,t), 3.44, 3.54(2H,dd,J= 10 Hz), 2.23(1H,d,J=11.2 Hz), 0.94(3H,d,J=5.6 Hz), 0.86 (3H,d,J=6.4 Hz), 0.73, 0.97, 1.07, 1.09, 1.42, 1.45(each 3H,s)

EXAMPLE 21

Preparation of methyl 2-deoxyasiatate(21)

Compound 20 (460 mg, 0.87 mmole) was added with tetrahydrofuran (10 ml) and 1N hydrochloric acid (1 ml) and stirred at room temperature for 5 hrs. The mixture was distilled under reduced pressure to completely remove the solvent. The residue was purified with column chromatography (hexane:ethyl acetate=3:2) to give white solid (402 mg, 95%). The crude product was recrystallized from ethyl acetate to give needle crystal.

$[\alpha]^{25}_D$;+69.6 (c=1.22, CHCl₃) IR(neat):3400, 1724 cm⁻¹ MS (EI):486(M⁺), 426, 262, 203, 133

EXAMPLE 22

Preparation of 2-deoxyasiatic acid (22)

Methyl 2-deoxyasiatate 21 (38 mg, 0.78 mmole) was added with LiI·3H₂O (450 mg, 2.39 mmole) and 2,4,6- collidine (5 mg) and heated for reflux for 10 hrs. During the reflux, a flask was wrapped with aluminum foil to prevent the light. The reaction mixture was concentrated under reduced pressure to remove collidine. The residue was purified with column chromatography (dichloromethane:methanol=20:1) to give pale yellow solid. The crude product was recrystallized from methanol to give needle crystal (280 mg, 76%).

IR (KBr): 3436,1693 cm$^{-1}$ MS (EI): 472(M+), 426, 248, 203, 133 $^1$H NMR (CDCl$_3$+pyridine-d$_5$) δ 5.21(1H,bt,J=2.8 Hz,3.6 Hz), 3.60(1H,t,J=7.2 Hz,8.2 Hz), 3.36, 3.70(2H,dd, J=10.0 Hz), 2.21(1H,d,J=11.2 Hz).

EXAMPLE 23

Preparation of methyl 2-O-benzyl-3,23-isopropylidene asiatate (23)

Sodium hydride (60% in mineral oil; 35 mg, 0.88 mmole) was washed with anhydrous hexane and added with a solution of methyl 3,23-O-isopropylidene asiatate 3 (240 mg, 0.44 mmole) and TBAI (20 mg) dissolved in anhydrous tetrahydrofuran. The mixture was stirred at room temperature for 20 mins, added with benzyl bromide (114 mg, 0.67 mmole) and heated for reflux for 2 hrs. After removing the solvent by distillation under reduced pressure, the mixture was treated with water (3 ml) and extracted with ethyl acetate (20 ml). The organic layer was washed with water (2ml×3), and a solution of saturated sodium chloride (3ml×3), and dried over anhydrous magnesium sulfate. The organic layer was concentrated under reduced pressure. The residue was purified with column chromatography (hexane:ethyl acetate=10:1) to give white solid (258 mg, 92%). The crude product was recrystallized from ethyl acetate to give needle crystal.

$[\alpha]^{23}{}_D$;+27.3(c=1.31, CHCl$_3$) IR(neat): 1724cm$^{-1}$ $^1$H NMR (CDCl$_3$) δ 7.24–7.33(5H,m), 5.25(1H,bt), 4.58, 4.80 (2H,dd,J=11.6 Hz), 3.62(3H,s), 3.60–3.50(4H,m), 2.23(1H, d,J=11.2 Hz), 1.46, 1.47(each 3H,s).

EXAMPLE 24

Preparation of 2-O-benzyl-3,23-O-isopropylidene asaticol (24)

Compound 23 (940 mg, 1.49 mmole) was dissolved in anhydrous ether (5 ml), added with lithium aluminum hydride (1.0M ether solution; 1.5 ml, 1.49 mmole) and heated for stirring for 1 hr. Water in small portions was added to the reaction mixture and then, produced aluminum hydride was filtered off. The organic layer was concentrated under reduced pressure. The residue was purified with column chromatography (hexane:ethyl acetate=1:3) to give white solid (890 mg, 99%).

$[\alpha]^{25}{}_D$;+32.6(c=1.17, CHCl$_3$) IR(neat): 3467 cm$^{-1}$ 7.25–7.35(5H, m), 5.14(1H, bt), 4.82(2H, ABq, J=12.0 Hz), 3.46–3.64(5H, m), 3.19(1H, d, J=11.2 Hz), 2.09 (1H, d), 1.47, 1.48(each 3H,s)

EXAMPLE 25

Preparation of 2α-benzyloxy-3β, 23-isopropylidenedioxyurs-12-ene-28-methanesulfonate (25)

Compound 24 (400 mg, 0.66 mmole) and triethyl amine (0.28 ml, 1.98 mmole) were dissolved in anhydrous dichloromethane (5 ml), added with methanesulfonyl chloride (76 ul, 0.99 mmole) at 0° C. and stirred for 30 mins. The mixture was distilled under reduced pressure to remove the solvent and extracted with ethyl acetate (20 ml). The organic layer was washed with water (30 ml×3) and a solution of saturated sodium chloride (3 ml×3), and dried over anhydrous magnesium sulfate. The organic layer was concentrated under reduced pressure. The residue was purified with column chromatography (hexane:ethyl acetate=2:1) to give white solid (430 mg, 95%).

$[\alpha]^{23}{}_D$;+23.4(c=1.28, CHCl$_3$) IR(neat): 1361, 1176 cm$^{-1}$ $^1$H NMR (CDCl$_3$) δ 7.25–7.35(5H,m), 5.17(1H,bt,J=2.8 Hz,3.6 Hz), 4.58, 4.81(2H,dd,J=11.6 Hz),3.74, 4.19(2H,dd, J=9.2 Hz), 3.48–3.71(4H,m), 2.96(3H,s), 1.46, 1.47(each 3H,s).

EXAMPLE 26

Preparation of 2α-benzyloxy-28-cyano-3β,23-isopropylidenedioxyurs-12-ene(26)

Compound 25 (500 mg, 0.73 mmole) and sodium cyanide (90%, 121 mg, 2.22 mmole) were dissolved in anhydrous dimethylform amide and heated for reflux for 12 hrs. The mixture was distilled under reduced pressure to completely remove the solvent and followed by the addition of ethyl acetate (10 ml) to dissolve produced nitrile and remove the salts by filtration. The organic layer was concentrated under reduced pressure. The residue was purified with column chromatography (hexane:ethyl acetate=5:1) to give white solid (383 mg, 85%).

$[\alpha]^{23}{}_D$;+27.7(c=1.13, CHCl$_3$) IR(neat): 2241 cm$^{-1}$ $^1$H NMR (CDCl$_3$) δ 7.22–7.27(5H,m), 5.20(1H,t), 4.54, 4.78 (2H,dd,J=11.6 Hz), 3.47–3.60(4H,m), 2.38(1H,d).

EXAMPLE 27

Preparation of 2α-benzyloxy-28-cyano-3β,23-dihydroxyurs-12-ene(27)

By the same procedure as described above for the preparation of Example 17 acetonid of compound 26 (95 mg, 0155 mmole) was deprotected to give white solid (85 mg, 96%).

IR(neat):3436, 2240 cm$^{-1}$ MS (EI):573(M$^+$), 482, 434, 331, 243, 203, 133, 91 $^1$H NMR (400 MHz, CDCl$_3$) δ 5.26(1H,bt), 4.46, 4.68(2H,AB quartet,J=11.2 Hz), 3.57(1H, m), 3.53(1H,d,J=9.2 Hz), 3.41, 3.67(2H,AB quartet,J=10.4 Hz), 2.09, 2.42(2H,AB quartet,J=16.4 Hz).

EXAMPLE 28

Preparation of 28-cyano-2α, 3β, 23-trihydroxyurs-12-ene (28)

Compound 27 (500 mg, 0.873 mmole) and 10% Pd/C (90 mg, about 3 mole %) were dissolved in methanol (10 ml) and the inside of flask was filled with hydrogen. The mixture was then stirred at ambient pressure for 8 hrs and Pd/C was filtered off. The reaction mixture was concentrated under reduced pressure to give white solid (420 mg, 99.6%).

IR(neat):3401, 2240 cm$^{-1}$ MS (EI):483(M$^+$), 465,447, 435,243,203,199,133 $^1$H NMR (400 MHz, CDCl$_3$) δ 5.25 (1H,bt), 3.77(1H,m) 3.69(1H,d,J=10.4 Hz), 3.43, 3.45(2H, AB quartet), 2.03, 2.45(2H,AB quartet,J=10.8 Hz).

EXAMPLE 29

Preparation of methyl 24-norurs-12-ene-3-one-28-oate(29)

Methyl 2-deoxyasiatate 14 (24 mg, 0.05 mmole) and pyridinium dichromate (56 mg, 0.15 mmole) were placed in a flask and the air was substituted with nitrogen. Then, by the addition of dichloromethane (4 ml), the mixture was stirred at room temperature for 5 hrs, filtered off by silica gel pad and concentrated under reduced pressure. The residue was purified with column chromatography to give white foaming solid (16 mg, 71%).

$^1$H NMR (CDCl$_3$) δ 5.27(1H,t), 3.62(3H,s), 2.46(1H,dt, J=12 Hz,J=6.8 Hz), 2.33–2.27(2H,m), 2.25(1H,d,J=12 Hz), 1.13, 1.07, 0.827(each 3H,s), 1.00(3H,d,J=6.4 Hz), 0.96(3H, d,J=10 Hz), 0.86(3H,d,J=6.8 Hz)

EXAMPLE 30

Preparation of methyl 3β-hydroxy-24-norurs-12-ene-28-oate $^1$H NMR (400 MHz, CDCl$_3$) δ 5.24(1H,t), 3.58(3H,s), 3.06(1H,dt), 2.21(1H,d,J=11.2 Hz), 1.24(3H,s), 1.05(3H,s), 0.95(3H,d,J=6.4 Hz), 0.84(3H,d,J=7 Hz), 0.84(3H,d,J=6.6 Hz), 0.75(3H,s)

EXAMPLE 31

Preparation of methyl 3β-hydroxy-3α-vinyl-24-norurs-12-ene-28-oate $^1$H NMR (400 MHz, CDCl$_3$) 5.79(1H,dd,J=12.2 Hz,J= 21.4 Hz), 5.24(1H,dd,J=1.4 Hz,J=21.4 Hz), 5.03(1H,dd,J= 1.4 Hz, J=12.2 Hz), 3.57(3H,s), 2.22(1H,d), 1.08(3H,s), 0.93(3H,s), 0.76(3H,s)

EXAMPLE 32

Preparation of methyl 3β-hydroxy-3α-methyl-24-norurs-12-ene-28-oate

Compound 29 (15 mg, 0.034 mmole) was dissolved in anhydrous tetrahydrofuran (4 ml) and added with methylmagnesium chloride (34 μl, 0.1 mmole) at room temperature. The mixture was stirred at the same temperature for 5 hrs and the reaction was stopped by the addition of water in small portions. The reaction mixture was filtered off and concentrated under reduced pressure. The residue was purified with column chromatography to give desired compound in 98% yield.

$^1$H NMR (400 MHz, CDCl$_3$) δ$^6$ 5.26(1H,t), 3.60(3H,s), 2.23(1H,d,J=11.2 Hz), 1.18(3H,s), 1.09(3H,s), 0.94(3H,d, J=6 Hz), 0.89(3H,d,J=6.8 Hz), 0.85(3H,s), 0.77(3H,s)

EXAMPLE 33

Preparation of methyl 3,23-isopropylidenedioxy-2-methoxyurs-2,12-diene-28-oate(33)

$^1$H NMR (400 MHz, CDCl$_3$) δ 5.30(1H,t), 3.62(3H,s), 3.56(1H,d,J=6 Hz), 3.54(3H,s), 2.27(1H,d), 1.53, 1.42, 1.26, 1.10, 1.04, 0.78(each 3H,s), 0.95(3H,d,J=6.4 Hz), 0.88(3H, d,J=4.4 Hz)

EXAMPLE 34

Preparation of methyl 23-hydroxy-2-methoxyurs-12-ene-3-one-28-oate(34)

$^1$H NMR (400 MHz, CDCl$_3$) δ 5.28(1H,t), 4.25(1H,dd, J=7.2 Hz, J=11.2 Hz), 3.60(3H,s), 3.40(3H,s), 2.26(1H,d,J= 12 Hz), 1.13(3H, s), 1.07(3H, s), 0.94(3H,d,J=6 Hz), 0.90 (3H,s), 0.87(3H,d,J=6.4 Hz)

EXAMPLE 35

Preparation of methoxymethyl 2,3,23-triacetylasiatate(35, R$_8$=H, R$_9$=methyl)

2,3,23-triacetylasiatic acid (300 mg, 0.49 mmole) was dissolved in dichloromethane (20 ml), added with diisopropylethyl amine (0.3 ml, 1.7 mmole) and then cooled. The mixture was stirred by the addition of chloromethyl ether (0.07 ml, 0.6 mmole) in small portions. After confirming the annihilation of a starting material, the reaction mixture was diluted with ethyl acetate. The organic layer was washed with 5% hydrochloric acid, water, a solution of saturated sodium bicarbonate and saturated brine in sequence. The solution was dried over anhydrous sodium sulfate and filtered off. The remaining solution was concentrated under reduced pressure. The residue was purified with column chromatography with hexane and ethyl acetate (5:1) to give desired compound as a solid (250 mg, 78%).

$^1$H NMR (300 MHz, CDCl$_3$) δ 5.28(1H,t,J=3.6 Hz), 5.21(1H,d,J=6 Hz), 5.17(1H,d,J=6 Hz), 5.18(1H,td,J=10.2 Hz,J=3.9 Hz), 5.08(1H,d,J=10.2 Hz), 3.86(1H,d,J=11.7 Hz), 3.58(1H,d,J=11.7 Hz), 3.45(3H,s), 2.28(1H,d,J=11.4 Hz), 2.09, 2.03, 1.98, 1.11, 1.09, 0.89, 0.79(each 3H,s), 0.96(3H, d,J=6.0 Hz), 0.86(3H,d,J=6.6 Hz), 2.0–1.0(20H,m)

EXAMPLE 36–46

By the similar procedure as described in Example 5, compounds were synthesized or by deprotecting compounds, so obtained, some compounds as shown in the following table 1 were prepared.

TABLE 1

| No | R$_1$ | R$_2$ | R$_3$ | R$_4$ | R$_5$ | NMR (400 MHz, CDCl$_3$, δ ppm) |
|---|---|---|---|---|---|---|
| 36 | —OH | —H | —OH | —OH | —CH$_2$OCH$_3$ | 5.28(1H, t, J=3.6Hz), 5.20(1H, d, J=6.0Hz), 5.16(1H, d, J=6.0Hz), 3.75(2H, m), 3.69(1H, d, J=10.5Hz), 3.45(3H, s), 3.42(1H, d, J=10.5Hz), 2.27(1H, d, J=11.4Hz), 1.10, 1.04, 0.96, 0.91, 0.79(each 3H, s), 0.95(3H, d, J=6.0Hz), 0.87(1H, d, J=6.3Hz), 2.2–0.8(23H, m) |
| 37 | AcO— | —H | AcO— | AcO— | BnOCH$_2$— | 7.34(5H, m), 5.32(2H, s), 5.28(1H, t, J=3.6Hz), 5.16(1H, dt, J=10.5Hz, 3.9Hz), 5.08(1H, d, J=10.5Hz), 4.68(2H, s), 3.86(1H, d, J=12Hz), 3.58(1H, d, J=12Hz), 2.27(1H, d, J=11.4Hz), 2.09, 2.03, 1.98, 1.09, 1.07, 0.89, 0.75(each 3H, s), 0.98(3H, d, J=6.0Hz), 0.86(3H, d, J=8.3Hz), 2.1–0.8(20H, m) |
| 38 | —OH | —H | —OH | —OH | BnOCH$_2$— | 7.33(5H, s), 5.31(3H, bs), 4.88(2H, s), 3.30–3.80(4H, m), 0.70–2.20(39H, m) |
| 39 | AcO— | —H | AcO— | AcO— | —CH$_2$O(CH$_2$)$_7$CH$_3$ | 5.27(1H, t, J=3.9Hz), 5.22(1H, s), 5.23(1H, s), 5.17(1H, td, J=10.2Hz, 3.9Hz), 5.08(1H, d, J=10.2Hz), 3.86(1H, d, J=11.7Hz), 3.58(1H, d, J=11.7Hz), 3.6(2H, m), 2.26(1H, d, J=11.1Hz), 2.08, 2.02, 1.98, 1.10, 1.08, 0.89, 0.78(each 3H, s), 0.95(3H, d, J=6.0Hz), 0.85(3H, d, J=3.6Hz), 2.0–0.8(35H, m) |

TABLE 1-continued

| No | $R_1$ | $R_2$ | $R_3$ | $R_4$ | $R_5$ | NMR (400 MHz, CDCl$_3$, δ ppm) |
|----|-------|-------|-------|-------|-------|-------------------------------|
| 40 | —OH | —H | —OH | —OH | —CH$_2$O(CH$_2$)$_7$CH$_3$ | 5.27(1H, t, J=3.6Hz), 5.24(1H, s), 5.23(1H, s), 3.77(1H, m), 3.69(1H, d, J=10.5Hz), 3.60(1H, t, J=6.6Hz), 3.59(1H, t, J=6.6Hz), 3.45(1H, d, J=10.5Hz), 3.42(1H, d, J=9.3Hz), 2.26(1H, d, J=11.1Hz), 1.10, 1.04, 0.91, 0.78(each 3H, s), 0.95(3H, d, J=5.7Hz), 0.88(3H, d, J=4.2Hz), 2.1–0.8(38H, m) |
| 41 | AcO— | —H | AcO— | AcO— | —CH$_2$OCH$_2$CH$_3$ | 5.28(1H, t, J=3.6Hz), 5.23(2H, s), 5.18(1H, dt, J=10.5Hz, 3.9Hz), 5.08(1H, d, J=10.5Hz), 3.85(1H, d, J=12Hz), 3.66(2H, q, J=7.2Hz), 3.57(1H, d, J=12Hz), 2.26(1H, d, J=11.1Hz), 2.08, 2.02, 1.97, 1.10, 1.08, 0.88, 0.78(each 3H, s), 1.21(3H, t, J=7.2Hz), 0.94(3H, d, J=6.0Hz), 0.85(3H, d, J=8.3Hz), 2.1–0.8(20H, m) |
| 42 | —OH | —H | —OH | —OH | —CH$_2$OCH$_2$CH$_3$ | 5.28(1H, t, J=3.3Hz), 5.24(2H, s), 3.8–3.6(2H, m), 3.67(q, J=7.2Hz), 3.45(1H, d, J=9.0Hz), 3.42(1H, d, J=9.0Hz), 1.23(3H, t, J=7.2Hz), 1.09, 0.91, 0.79(each 3H, s), 0.95(3H, d, J=5.7Hz), 0.86(3H, d, J=6.6Hz), 2.0–1.0(23H, m) |
| 43 | AcO— | —H | AcO— | AcO— | —CH$_2$OCH$_2$CH$_2$OCH$_3$ | 5.28(2H, s), 5.1–5.3(3H, m), 3.4–3.8(6H, m), 3.39(2H, s), 2.2(1H, d, J=11Hz), 2.09, 2.02, 1.98, 1.10, 0.78(each 3H, s), 1.16(6H, s). 0.89(6H, s), 2.0–1.0(20H, m) |
| 44 | —OH | —H | —OH | —OH | —CH$_2$OCH$_2$CH$_2$OCH$_3$ | 5.27(2H, s), 5.2(1H, m), 3.7–3.3(8H, m), 3.39(3H, s), 2.2(1H, d, J=11Hz), 1.09, 1.04, 0.95, 0.77(each 3H, s), 0.90(6H, s), 2.0–1.0(23H, m) |
| 45 | AcO— | —H | AcO— | AcO— | —CH(OCH$_2$CH$_3$)CH$_3$ | 5.84(1H, q, J=5.0Hz), 5.10–5.27(3H, m), 3.40–3.90(4H, m), 2.08, 2.02, 1.97(each 3H, s), 0.73–2.10(46H, m) |
| 46 | —OH | —H | —OH | —OH | —CH(OCH$_2$CH$_3$)CH$_3$ | 5.86(1/2H, q, J=5.1Hz), 5.84(1/2H, q, J=5.1Hz), 5.28(1H, t, J=2.7Hz), 5.17(1H, dt, J=10.2Hz, 4.5Hz), 5.09(1H, d, J=10.2Hz), 3.86(1H, d, J=11.7Hz), 3.70(1H, m), 3.58(1H, d, J=11.7Hz), 3.50(1H, m), 2.27(1H, d, J=11.1Hz), 2.09, 2.03, 1.98, 1.11, 1.09, 0.89, 0.80(each 3H, s), 1.37(3/2H, d, J=5.1Hz), 1.33(3/2H, d, J=5.1Hz), 1.20(3H, m), 0.95(3H, d, J=5.7Hz), 0.85(3H, dd, J=6.5Hz, 1.5Hz), 2.1–0.8(23H, m) |

EXAMPLE 47

Preparation of 2'-tetrahydropyranyl-2,3,23-triacetylasiatate (37, $R_{10}$-$R_{11}$=—CH$_2$CH$_2$CH$_2$—)

2,3,23-triacetylasiatic acid (1150 mg, 1.88 mmole) was dissolved in dichloromethane (15 ml), added with 3,4-dihyro-2H-pyran (0.68 ml, 7.52 nmole), and then cooled. The mixture was stirred by the addition of p-toluenesulfonic acid (10 mg) for 12 hrs. The reaction mixture was diluted with ethyl acetate, dried over anhydrous sodium sulfate and filtered off. The remaining solution was concentrated under reduced pressure. The residue was purified with column chromatography with hexane and methanol (20:1) to give desired compound as white powder (1185 mg, 90%).

$^1$H NMR (400 MHz, CDCl$_3$) δ 5.88(1/2H,m), 5.84(1/2H, m), 5.20(1H,m), 5.09(td,J=4 Hz,J=10 Hz,), 5.01(1H,d,J=10 Hz), 3.80(1H,m), 3.78(1H,d,J=12 Hz), 3.60(1H,m), 3.52 (1H,d,J=12 Hz), 2.22(1/2H,d,J=11 Hz), 2.19(1/2H,d,J=11 Hz), 2.02, 1.95, 1.91, 1.03, 1.02, 0.81(each 3H,s), 0.88(3H, d,J=6 Hz), 0.79(3H,d,J=6.4 Hz), 0.71(3H,d,J=3.6 Hz), 2.0–1.0(26H,m)

EXAMPLE 48–54

By the similer procedure as described in example 47 and by deprotecting the hydroxy s of compounds, so obtained, some compounds (48–52) as shown in the following table 2 were prepared. The compounds 53 and 54 were prepared based upon said Example 35 or upon deprotecting the hydroxy s of the compounds, so obtained, with potassium carbonate.

TABLE 2

| No | $R_1$ | $R_2$ | $R_3$ | $R_4$ | $R_5$ | NMR(400 MHz, CDCl$_3$, δ ppm) |
|----|-------|-------|-------|-------|-------|-------------------------------|
| 48 | —OH | —H | —OH | —OH | (tetrahydropyranyl-O-) | 5.94(1/2H, s, br), 5.93(1/2H, s, br), 5.29(1/2H, t, J=3.8Hz), 5.26(1/2H, t, 3.6Hz), 3.89(1H, dt, J=10.2Hz, 2.7Hz), 3.88(1H, d, J=10.5Hz), 3.5(2H, m), 3.43(1H, d, J=10.2Hz), 3.41(1H, d, J=10.5Hz), 2.28(1/2H, d, J=11.1Hz), 2.27(1/2H, d, J=11.1Hz), 1.06, 1.03, 0.89(each 3H, s), 0.95(3H, d, J=6.6Hz), 0.87(3H, d, J=6.6Hz), 0.78(3/2H, s), 2.1–0.8(29H, m) |
| 49 | —OH | —H | —OH | —OH | (triacetyl sugar-O-) | 5.55(1H, d), 5.1–5.3(4H, m), 3.8–3.4(5H, m) 4.2–4.0(2H, m), 3.0–2.6(3H, m), 2.1–1.8(12H, m), 2.0–0.7(40H, m) |

TABLE 2-continued

| No | $R_1$ | $R_2$ | $R_3$ | $R_4$ | $R_5$ | NMR(400 MHz, CDCl$_3$, δ ppm) |
|---|---|---|---|---|---|---|
| 50 | AcO— | —H | AcO— | AcO— | (tetraacetyl sugar structure with O, OAc, AcO, AcO, OAc) | |
| 51 | AcO— | —H | AcO— | AcO— | (acetyl sugar structure with O, OAc, OAc, OAc) | 5.54(1H, d, J=8.0Hz), 5.30(1H, t, J=3.3Hz), 5.4–5.0(5H, m), 4.28(1H, dd, J=4.4Hz, J=12.4Hz), 4.03(1H, dd, J=2.0Hz, J=12.4Hz), 3.87(1H, d, J=11.8Hz), 3.78(1H, ddd, J=2.0Hz, J=4.4Hz, J=12.0Hz), 2.20(1H, d, J=11Hz), 2.09, 2.07, 1.99, 1.10, 1.07, 0.96, 0.89, 0.77(each 3H, s), 2.03(6H, s), 2.02(6H, s), 0.85(3H, d, J=6.5Hz), 2.0–1.0(20H, m) |
| 52 | AcO— | —H | AcO— | AcO— | (tetrahydrofuran ring with O) | 6.23(1H, t, J=3.2Hz), 5.25(1H, m), 5.17(1H, td, J=3.9Hz, 10.2Hz), 5.09(1H, d, J=10.2Hz), 3.9(2H, m), 3.86(1H, d, J=12Hz), 3.58(1H, d, J=12Hz), 2.21(1H, d, J=11Hz), 2.09, 2.03, 1.98, 1.11, 1.08, 0.95, 0.89(each 3H, s), 0.85(3H,d, J=6.4Hz), 0.82(3H, d, J=3.3Hz), 2.30–0.80(25H, m) |
| 53 | AcO— | —H | AcO— | AcO— | —CH(OC$_4$H$_9$)CH$_3$ | 5.82(½H, q, J=3.6Hz), 5.80(½H, q, J=3.6Hz), 5.28(1H, m), 5.15(1H, td, J=3.9Hz, 9.6Hz), 5.07(1H, d, J=10.5Hz), 3.85(½H, d, J=11.7Hz), 3.84(½H, d, J=11.7Hz), 3.56(½H, d, J=11.7Hz), 3.55(½H, d, J=11.7Hz), 3.65(1H, m) 3.40(1H, m), 2.26(½H, d, J=11.7Hz), 2.25(½H, d, J=11.7Hz), 2.07, 2.01, 1.96(each 3H, s), 2.0–0.7(45H, m) |
| 54 | —OH | —H | —OH | —OH | —CH(OC$_4$H$_9$)CH$_3$ | 5.83(1H, m), 5.28(1H, m), 3.7(3H, m), 3.4(3H, m), 2.45(1H, d, J=7.4Hz), 2.4–0.7(51H, m) |

EXAMPLE 55

Preparation of methyl 2-O-methylasiatate (41,R3=methyl)

$^1$H NMR (400 MHz, CDCl$_3$) δ 5.26(1H,t,J=3.6 Hz), 3.24–3.32(1H,m) 2.24(d,J=11.2 Hz), 3.60, 3.39, 1.07, 1.03, 0.92, 0.75,(each 3H,s), 0.94(3H,d,J=5.8 Hz), 0.85(3H,d,J=6.4 Hz)

EXAMPLE 56

Preparation of methyl 3,23-diacetyl-2-O-methyl-11-oxoasiatate(42, R$_3$=methyl)

Compound 41 (R3=methyl, 400 mg) and DMAP (30 mg) were placed in a flask and the air was substituted into nitrogen. Then, by the addition of tetrahydrofuran (10 ml) and acetic anhydride (1 ml) in sequence, the mixture was stirred at room temperature for 1 hr. After confirming the progress of the reaction by TLC, methanol (10 ml) was added to the reaction mixture and followed by concentration under reduced pressure. Sodium dichromate (460 mg) was added to the reaction mixture and followed by the addition of acetic acid (20 ml). The reaction mixture was heated for reflux in oil bath for 2 hrs and the progress of the reaction was confirmed by TLC. Acetic acid was filtered off under reduced pressure. The residue was extracted with ethyl acetate and then, the organic layer was washed with water five times and concentrated under reduced pressure. A desired compound was obtained as white solid.

$^1$H NMR (400 MHz, CDCl$_3$) δ 5.63(1H,s), 4.95(1H,d,J=10 Hz), 3.80, 3.56(2H,ABq,J=11.6 Hz), 3.40–3.48(1H,m), 3.61, 3.33, 1.30, 1.23, 0.90, 0.85(each 3H,s), 2.06(6H,s), 0.97(3H,d,J=6.4 Hz), 0.87(3H,d,J=6.8 Hz), 2.43(1H,d,J=11.2 Hz)

EXAMPLE 57

Preparation of methyl 2-O-methyl-11-oxoasiatate (43, R$_3$=methyl)

$^1$H NMR (400 MHz, CDCl$_3$) δ 5.63 (1H, s), 3.62, 3.41, 1.31, 1.20, 0.92, 0.89 (each 3H, s), 2.42 (1H, d), 0.98 (3H, d, J=7 Hz), 0.87 (3H, d, J=6.4 Hz)

EXAMPLE 58

Preparation of methyl 2-O-ethyl asiatate(43, R$_3$=ethyl)

$^1$H NMR (400 MHz, CDCl$_3$) δ 5.26(1H,t), 3.61(3H,s), 2.23(1H,d), 1.20(3H,t,J=6.8 Hz), 0.94(3H,d,J=6.4 Hz), 0.85 (3H,d,J=6.4 Hz), 0.75, 0.90, 1.04, 1.56(each 3H,s)

EXAMPLE 59

Preparation of methyl 2-O-ethyl-11-oxoasiatate(43, R$_3$=ethyl)

$^1$H NMR (400 MHz, CDCl$_3$) δ 5.61 (1H, s), 3.61 (3H, s), 2.41 (1H, d), 1.19 (3H, t, J=6.8 Hz), 0.97, (3H, d, J=6.0 Hz), 0.86 (3H, d, J=6.8 Hz), 0.89, 0.91, 1.23, 1.30 (each 3H, s)

EXAMPLE 60

Synthesis of methyl 2-O-acetyl asiatate(44)

$^1$H NMR (400 MHz, CDCl$_3$) δ 5.24(1H,t,J=3.6 Hz), 4.97–5.03(1H,m), 3.60(3H,s), 2.23(1H,d,J=11.6 Hz), 2.02 (3H,s), 1.08(3H,d,J=6.0 Hz), 0.84(3H,d,J=6.4 Hz), 0.75, 0.90, 1.07, 1.09(each 3H,s)

EXAMPLE 61

Synthesis of methyl 2α-acetyl-3β-hydroxyurs-12-ene-23-a1-28-oate(45)

Compound 44 (300 mg, 0.55 mmole) and pyridinium dichromate (PDC; 413 mg, 2 equivalents) were placed in a flask and the air was substituted into nitrogen. Then, said materials were dissolved in dichloromethane (9 ml) and stirred at room temperature for 3 hrs. After confirming the end of the reaction by TLC, isopropanol (1 ml) was added to the reaction mixture and eluted with ethyl acetate on silica gel short column to remove the mineral material. The solution, so obtained, was dried over anhydrous magnesium sulfate and concentrated under reduced pressure. The residue was purified with silica gel column chromatography with hexane and ethyl acetate (10:1) to give desired compound as white solid (150 mg, 53%).

$^1$H NMR (400 MHz, CDCl$_3$) δ 9.40(1H,s), 5.25(1H,t,J=4 Hz), 4.99–5.05(1H,m), 3.60(3H,s), 2.24(1H,d,J=12 Hz), 2.08(3H,s), 0.94(3H,d,J=6 Hz), 0.85(3H,d,J=6.4 Hz), 0.75, 1.09, 1.11, 1.29(each 3H,s)

EXAMPLE 62

Synthesis of methyl 2α-acetylurs-12-ene-23-al-3-one-28-oate(45)

$^1$H NMR (400 MHz, CDCl$_3$) δ 9.43(1H,s), 5.47–5.55(1H, m), 5.27(1H,t), 3.61(3H,s), 2.25(1H,d,J=11 Hz), 2.13(3H,s), 0.94(3Hd,J=6.4 Hz), 0.86(3H,d,J=6.4 Hz), 0.82, 1.10, 1.33, 1.34(each 3H, s)

EXAMPLE 63

Synthesis of methyl 2α-benzyl-3β,23-dihydroxyurs-12-ene-28-oate(47)

$^1$H NMR (400 MHz, CDCl$_3$) δ 7.27–7.36(5H,m), 4.68, 4.44(2H,ABq,J=11.2 Hz), 3.61(3H,s), 2.21(1H,d), 1.08, 1.03, 0.90, 0.75(each 3H,s), 0.94(3H,d,J=5.8 Hz), 0.86(3H, d,J=6.4 Hz)

EXAMPLE 64

Synthesis of methyl 2α-benzyl-3β-hydroxyurs-12-ene-23-al-28-oate(48)

$^1$H NMR (400 MHz, CDCl$_3$) δ 9.35(1H,s), 7.29–7.36(5H, m), 5.27(1H,t), 4.69, 4.46(ABq,2H,J=11.2 Hz), 3.60(3H,s), 2.25(1H,d), 1.11, 1.09, 1.04, 0.75(each 3H,s) 0.95(3H,d,J= 6.4 Hz), 0.91(3H,d,J=6.0 Hz)

EXAMPLE 65

Preparation of 2α-benzyloxy-3β,23-hydroxyurs-12ene-28-carboxylic acid (49)

$^1$H NMR (400 MHz, CDCl$_3$) δ 7.30–7.40(5H,m), 5.21 (1H,t), 4.70, 4.47(2H,ABq,J=11.6 Hz), 3.67, 3.43(2H,ABq, J=10.8 Hz), 2.28(1H,t,J=13.7 Hz), 1.13, 1.08, 1.05, 0.94 (each 3H,s), 0.93(3H,d,J=8.8 Hz), 0.82(3H,d,J=6.4 Hz)

EXAMPLE 66

Preparation of 2α,3β,23-trihydroxyurs-12-ene- 28-carboxylic acid (50, 28-homoasiatic acid)

$^1$H NMR (400 MHz, CDCl$_3$) δ 5.17(1H,t,J=3.4 Hz), 3.87–3.93(1H,m), 3.82, 3.70(2H,ABq,J=10.3 Hz), 3.50(1H, d,J=7.8 Hz), 2.43(1H,d,J=13.2 Hz), 1.98, 1.89(2H,ABq,J= 13.2 Hz), 1.08, 1.06, 1.02, 0.93(each 3H,s), 0.92(3H,d,J=8.8 Hz), 0.81(3H,d,J=6.4 Hz)

EXAMPLE 67

Preparation of 3,23-O-isopropylidene-2-oxoasiatic acid (51)

$^1$H NMR (400 MHz, CDCl$_3$) δ 5.23(1H,m), 4.39(1H,bs), 3.62(1H,bs), 3.49(1H,bs), 2.62(1H,s), 1.50(3H,s), 1.44(3H, s), 1.24(3H,s), 1.13(3H,s) 1.01(3H,s), 0.95–0.85(6H,m), 0.75(3H,s)

EXAMPLE 68–69, 71–73 AND EXAMPLE 75–80

By the similar procedure as described in Example 35 or 47, compounds were synthesized or by deprotecting the hydroxy s of compounds, so obtained, in a common method, compounds as shown in the following table 3 were prepared.

TABLE 3

| No | R$_1$ | R$_2$ | R$_3$ | R$_4$ | R$_5$ | NMR(400 MHz, CDCl$_3$, δ ppm) |
|---|---|---|---|---|---|---|
| 68 | —O | —O | —OC(CH$_3$)$_2$O— | | —CH$_2$OCH$_2$CH$_3$ | 5.26(1H, t), 5.23(2H, s), 4.40(1H, s), 3.56–3.72(4H, m), 2.40(1H, d, J=12Hz), 2.53, 2.27(2H, ABq, J=10.4Hz), 1.54, 1.52, 1.15, 1.05, 1.01, 0.78(each 3H, s), 1.22(3H, t, J=6Hz), 1.01(3H, d) 0.87(3H, d, J=5.2Hz) |
| 69 | —O | —O | —OC(CH$_3$)$_2$O— | | —CH$_2$O(CH$_2$)$_7$CH$_3$ | 5.26(1H, t), 5.23(2H, q, J=6Hz), 4.40(1H, s) 3.55–3.72(4H, m), 2.27(1H, d), 2.40, 2.10(ABq, J=12Hz), 1.53, 1.46, 1.10, 1.06, 1.01, 0.77(each 3H, s), 0.95(3H, d, J=5.8Hz), 0.87(3H, d, J=6.4Hz) |
| 71 | —OH | —H | —OC(CH$_3$)$_2$O— | | —CH$_2$OCH$_2$CH$_3$ | 5.27(1H, t), 5.23(2H, s), 3.74–3.82(1H, m), 3.66(2H, q, J=7.6Hz), 3.53, 3.44(2H, ABq), 3.32(1H, d, J=9.6Hz), 2.25(1H, d), 1.46, 1.44(2H, ABq), 1.10, 1.07, 1.03, 0.76(each 3H, s), 1.22(3H, t, J=6.8Hz), 0.95(3H, d, J=5.6Hz), 0.86(3H, d, J=6.4Hz) |
| 72 | —OH | —H | —OC(CH$_3$)$_2$O— | | —CH$_2$O(CH$_2$)$_7$CH$_3$ | 5.30(2H, s), 5.26(1H, t), 3.73–3.82(1H, m), 3.32(1H, d, J=9.6Hz), 2.25(1H, d), 1.46, 1.45, 1.10, 1.07, 1.04, 0.76(each 3H, s) |
| 73 | AcO— | —H | —OC(CH$_3$)$_2$O— | | 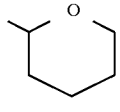 | 5.91(1H, t), 5.23(1H, t), 4.96–5.02(1H, m), 3.68(1H, d), 3.54, 3.50(2H, Abq, J=13.4Hz), 2.28(1H, d), 2.01, 1.43, 1.41, 1.12, 1.10, 1.08, 0.75(each 3H, s) |
| 75 | —H | —H | AcO— | AcO— | 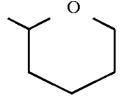 | 5.96(1/2H, s), 5.92(1/2H, s), 5.29(1/2H, t), 5.26(1/2H, t), 3.88, 3.69(2H, ABq, J=4.8Hz), 2.06, 2.02, 1.09, 0.98, 0.83(each 3H, s) |
| 76 | —H | —H | —OH | —OH | —CH$_2$OCH$_2$CH$_3$ | 5.26(1H, t, J=3.6Hz), 5.23(2H, s), 3.73, 3.43(2H, ABq, J=10.3Hz), 3.66(2H, q, J=6.84Hz), 2.25(1H, d, J=11.24Hz), 1.22(3H, t, J=7.08Hz), 1.08, 0.89, 0.78(each 3H, s), 0.96(3H, d, J=6.81Hz), 0.86(3H, d, J=6.4Hz) |
| 77 | —H | —H | —OH | —OH | —CH$_2$O(CH$_2$)$_7$CH$_3$ | 5.26(1H, t, J=3.4Hz), 5.23(2H, s), 3.72, 3.44(2H, ABq, J=10.4Hz), |

TABLE 3-continued

| No | R₁ | R₂ | R₃ | R₄ | R₅ | NMR(400 MHz, CDCl₃, δ ppm) |
|---|---|---|---|---|---|---|
| 79 | —H | —OH | —H | —OH | —CH₂O(CH₂)₇CH₃ | 3.53–3.67(3H, m), 2.25(1H, d, J=11.2Hz), 1.08, 0.97, 0.89, 0.78(each 3H, s), 0.96(3H, d, J=5.4Hz), 0.87(3H, d, J=5.4Hz) 5.29(1H, t, J=3.2Hz), 5.23(2H, s), 4.11–4.20(1H, m), 3.37 3.18(2H, ABq, J=10.8Hz), 2.26(1H, d, J=11.4Hz), 1.24, 1.09, 0.98, 0.80(each 3H, s) |
| 80 | —H | AcO— | —H | AcO— | 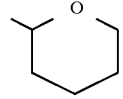 | 3.88, 3.70(2H, ABq, J=10.8Hz), 2.08, 2.02, 1.18, 1.09, 1.01, 0.79(each 3H, s), 0.86(3H, d, J=7.3Hz) |

EXAMPLE 70

Preparation of 2-O-acetyl-3,23-O-isopropylidene asiatic acid (54)

¹H NMR (400 MHz, CDCl₃) δ 5.23(t,1H,J=3.6 Hz), 4.96–5.03(m,1H), 3.67, 3.42(AB q,2H,J=10.8 Hz), 3.65(d, 1H,J=9.8 Hz), 2.18(d,1H,J=11.7 Hz), 2.09, 1.09, 1.08, 0.88, 0.78(each S, 3H), 0.94(d, 3H,J=6 Hz), 0.84(d,3H,J=6.8 Hz)

EXAMPLE 74

Preparation of 2-deoxy-3,23-O-diacetylasiatic acid (60)

¹H NMR (400 MHz, CDCl₃) δ 5.25(1H,s), 4.79(1H,t), 3.88, 3.70(AB q,2H,J=11.2 Hz), 2.19(1H,d,J=10.8 Hz), 2.03, 2.06, 1.08, 0.99, 0.86, 0.78(each s, 3H), 0.86(d,3H,J=5.6 Hz)

EXAMPLE 78

Preparation of 2, 23-diacetylurs-12-ene-28-oic acid (68)

¹H NMR (400 MHz, CDCl₃) δ 5.26(1H,t), 5.17(1H,t,J=9.2 Hz), 3.89, 3.69(2H,ABq,J=10.8 Hz), 2.19(1H,d,J=10.8 Hz), 2.08, 2.02, 1.20, 1.08, 0.99, 0.79(each 3H,s), 0.95(3H, d,J=6.4 Hz), 0.85(3H,d,J=6.8 Hz)

EXAMPLE 81

Preparation of methyl 2α-azidoasiatate(74)

¹H NMR (400 MHz, CDCl₃) δ 5.25(1H,m), 3.65–3.39 (4H,m), 3.55(3H,s), 1.18(3H,s), 1.05(3H, s), 0.98(3H,s), 0.94(3H,m,J=5.0 Hz), 0.86(3H,m,J=8.0 Hz), 0.75 (3H,s).

EXAMPLE 82

Preparation of methyl 2α-thiophenoxyasiatate(75)

m.p.: 229°–233° C.

EXAMPLE 83

Preparation of methyl 3β-hydroxy-23-undecylenyloxyurs-12-ene-28-oate (76)

Compound 14 (200 mg, 0.41 mmole), so obtained from Example 13, and DCC (93.4 mg, 0.45 mmole) were dissolved in dichloromethane (15 ml). Then, undecylenic acid (83.4 mg, 0.45 mmole) and dimethylaminopyridine (40.2 mg, 0.33 mmole) were added to the mixture at 0° C. and stirred under nitrogen atmosphere at room temperature for 2 hrs. The reaction mixture was filtered on celite. The remaining solution was concentrated under reduced pressure and followed by the addition of water. The organic layer was extracted with ethyl acetate, washed with 10% hydrochloric acid, a solution of saturated sodium carbonate, water, and a solution of saturated sodium chloride, and then, dried over anhydrous magnesium sulfate. The remaining solution was concentrated under reduced pressure. The residue was purified with column chromatography with hexane and ethyl acetate (2:1) to give desired compound as an oil (225 mg, 85%).

EXAMPLE 84

Preparation of methyl 2β, 3β-epoxy-23-undecylenyloxyurs-12-ene-28-oate(77)

¹H NMR (400 MHz, CDCl₃) δ 5.80(1H,m), 5.27(1H,m), 4.99(1H,d,J=17.0 Hz), 4.93(1H,d, −74 J=12.3 Hz), 4.10(1H, d,J=11.1 Hz), 3.88(1H,d,J=11.1 Hz),3.60(3H,s), 3.25(1H, bs), 3.04(1H,d,J=3.2 Hz).

EXAMPLE 85

Preparation of dimethyl 2β, 3β-epoxyurs-12-ene-23, 28-dioate(79)

¹H NMR (400 MHz, CDCl₃) δ 5.26(1H,m), 3.75(3H,s), 3.60(3H,s), 3.30(1H,d,J=3.8 Hz), 3.19(1H,d,J=3.9 Hz), 1.25 (3H,s), 1.09(3H,s), 1.06(3H,s), 0.94(3H,d,J=5.2 Hz), 0.86 (3H,d,J=8.0 Hz), 0.72(3H,s).

Preparation of crude product (compound 78)

¹H NMR (400 MHz, CDCl₃) δ 5.27(1H,m), 3.60(3H,s), 3.32(1H,d,J=3.8 Hz), 3.28–3.27(1H,m), 1.24 (3H,s), 1.10 (3H,s), 1.06(3H,s), 0.94(3H,d,J=5.3 Hz), 0.86(3H,d,J=6.4 Hz), 0.73(3H,s).

EXAMPLE 86

Preparation of methyl 2β, 3β-epoxyurs-12-ene-23-N-phenylamido-28-oate(80)

¹H NMR (400 MHz, CDCl₃) δ 8.10(1H,d,J=8.5 Hz), 7.61–7.55(1H,m), 7.49–7.43(1H,m), 7.35(1H,d,J=8.5 Hz), 5.29(1H,m), 3.62–3.60(1H,m), 3.60(3H,s), 3.50–3.47(1H, m), 1.25(3H,s), 1.19(3H,s), 1.11(3H,s), 0.94 (3H, d, J=6.0 Hz), 0.86(3H,d,J=6.4 Hz), 0.78(3H,s).

Experiment 1

Wound healing properties of the present invention
Preparation of an ointment 200 mg of a compound of the present invention, accurately weighed, was put into a syringe (20 ml). Then, propylene glycol (6 g), glycol stearate (3 g) and white petriatum (1 g), accurately weighed, were put into said syringe. The syringe was immersed in water bath 80° C. to completely melt the contents. It was agitated for about 5 mins so that active ingredients may be homogeneously dispersed to said 3 bases. Another syringe to put purified water (10 g) heated at 80° C. was prepared. By connection of two syringes to a threeway connector, the input at both sides was repeated about 20 times so that the contents were homogenized. The homogenized contents were put into a container and solidified slowly at room temperature.

Method

To evaluate the wound healing effects related to newly synthesized asiaticoside derivatives and naturally separated asiaticoside, asiatic acid and madecassic acid, rats were given wounds. Among several methods to measure the wound healing effects based upon a rationale that the wound lesions associated with trauma or necrosis are cured by tissue regeneration such as exuberant granulation, etc., the tensile strength method is derived from the fact that tensile strength is evenly increased until a recovered site of wounded tissue is to be recleaved and under pulling at both sides. the force until the wound site is cleaved is measured. Meantime, it has been noted that the tensile strength method in cleaved wounds reflects the quality and speed of regeneration very well.

The following table, using said tensile strength method, compared the wound healing effects between TECA (titrated extracted *Centella asiatica*), one of the active ingredients of currently marketed madecassol ointment and newly synthesized asiaticoside derivatives.

The wound healing effects of new asiaticoside derivatives

| Test Compounds | Tensile Strength (g ± S.E.) | % increase from TECA |
|---|---|---|
| Compound 5 (R = H) | 348.75 ± 64.79 | −23.8 |
| Compound 22 | 386.25 ± 25.06 | −15.6 |
| TECA | 457.50 ± 45.24 | |
| Compound 7 (R = H) | 345.00 ± 29.74 | −0.3 |
| Compound 7 (R = CH$_3$) | 383.00 ± 28.78 | 10.7 |
| Compound 5 (R = CH$_3$) | 357.00 ± 21.54 | 3.2 |
| TECA | 346.00 ± 22.64 | |
| Compound 14 | 520.00 ± 46.94 | 7.7 |
| Compound 10 | 321.25 ± 26.66 | −3.3 |
| Compound 15 | 506.25 ± 41.57 | 4.9 |
| TECA | 482.50 ± 42.71 | |
| Compound 12 | 306.25 ± 26.69 | −20.7 |
| Compound 16 | 303.75 ± 32.01 | −21.4 |
| Compound 74 | 316.25 ± 25.24 | −18.1 |
| Compound 41 (R$_3$ = CH$_3$) | 331.25 ± 20.19 | −14.2 |
| Compound 43 (R$_3$ = CH$_3$) | 392.50 ± 27.83 | 1.6 |
| TECA | 386.25 ± 41.11 | |
| Compound 41 (R$_3$ = C$_2$H$_5$) | 355.00 ± 52.35 | 4.8 |
| Compound 43 (R$_3$ = C$_2$H$_5$) | 405.00 ± 43.59 | 19.6 |
| Compound 2a | 416.25 ± 23.58 | 22.9 |
| Compound 2b | 452.50 ± 43.86 | 33.6 |
| TECA | 338.75 ± 30.38 | |
| Compound 75 | 418.75 ± 32.51 | −2.9 |
| Compound 78 (R$_5$ = OH) | 368.57 ± 30.85 | −14.5 |
| Compound 79 (R$_5$ = OMe) | 367.50 ± 56.12 | −14.8 |
| Compound 77 | 362.50 ± 32.90 | −15.9 |
| TECA | 431.11 ± 42.09 | |
| Compound 76 | 391.25 ± 40.75 | 4.7 |
| Compound 18 (R' = CH$_3$) | 277.78 ± 14.72 | −25.7 |
| Compound 18 (R' = C$_2$H$_5$) | 297.50 ± 25.66 | −20.4 |
| TECA | 373.75 ± 23.45 | |
| Compound 45 | 287.50 ± 2.83 | −4.2 |
| Compound 53 | 351.15 ± 49.51 | 17.1 |
| Compound 52 | 303.75 ± 17.49 | 1.3 |
| Compound 64 | 336.25 ± 31.02 | 12.1 |
| Compound 61 | 360.00 ± 21.58 | 20.0 |
| Compound 59 | 323.75 ± 47.37 | 7.9 |

-continued

| Test Compounds | Tensile Strength (g ± S.E.) | % increase from TECA |
|---|---|---|
| Compound 58 | 327.50 ± 40.96 | 9.2 |
| Compound 57 | 320.00 ± 28.50 | 6.7 |
| TECA | 300.00 ± 34.68 | |
| Compound 38 (R$_{10}$–R$_{11}$ = —CH$_2$CH$_2$CH$_2$—) | 488.89 ± 33.05 | 21.55 |
| Compound 36 (R$_8$ = H, R$_9$ = octyl) | 396.00 ± 26.43 | −1.55 |
| Compound 36 (R$_8$ = H, R$_9$ = ethyl) | 410.00 ± 32.32 | 1.93 |
| Compound 37 (R$_{10}$–R$_{11}$ = —CH$_2$CH$_2$CH$_2$—) | 426.67 ± 22.50 | 6.08 |
| Compound 35 (R$_8$ = H, R$_9$ = ethyl) | 538.00 ± 38.75 | 33.76 |
| TECA | 402.22 ± 27.48 | |

We claim:

1. An asiatic acid derivative of formula I

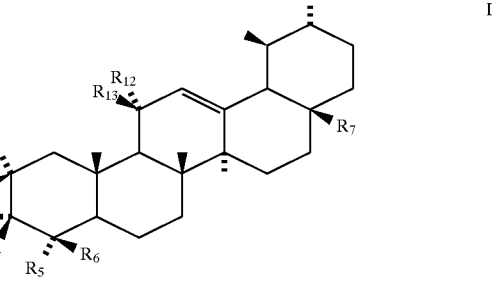

or a pharmaceutically acceptable salt or ester thereof, wherein:

R$_1$ is selected from the group consisting of hydrogen, hydroxy, methyl, ethyl, methoxy, ethoxy, vinyl, ethynyl, cyano, azaide, methanesulfonyloxy, phenylthio, and (methylthio) thiocarbonyloxy, wherein said hydroxy may be protected by acetyl or benzyl;

R$_2$ is selected from the group consisting of hydrogen, hydroxy, methoxy, and ethoxy, wherein said hydroxy may be protected by acetyl or benzyl; or R$_1$ and R$_2$ may form oxo altogether;

R$_3$ is selected from the group consisting of hydrogen, hydroxy, vinyl, methyl, and ethyl, wherein said hydroxy may be protected by acetyl or benzyl;

R$_4$ is selected from the group consisting of hydrogen, methyl, ethyl, vinyl, and hydroxy, wherein said hydroxy may be protected by acetyl or benzyl; or R$_2$ and R$_4$ may form epoxy altogether; or R$_3$ and R$_4$ may form oxo altogether;

R$_5$ is selected from the group consisting of methyl, hydroxymethyl where hydroxy may be protected by acetyl or benzyl, tert-butyldimethylsilyloxymethyl, carboxyl, carboxylester, carboxylamide, and aldehyde; or R$_4$ and R$_5$ may form —OC(CH$_3$)$_2$OCH$_2$— altogether;

R$_6$ is selected from the group consisting of hydrogen and methyl;

R$_7$ is selected from the group consisting of —CH$_2$COOR, —COOR, hydroxymethyl where hydroxy may be protected by acetyl or benzyl, methanesulfonyloxymethyl, and cyanomethyl, wherein:

R is hydrogen, methyl, CH(OR$_9$)R$_8$, CH(OR$_{11}$)CH$_2$R$_{10}$, or glucosyl or rhamnosyl where hydroxy may be protected by acetyl or benzyl;

R$_8$ is selected from the group consisting of hydrogen, methyl and ethyl;

R$_9$ is selected from the group consisting of methyl, ethyl, octyl, benzyl, methoxymethyl, and methoxyethyl;

R$_{10}$ is selected from the group consisting of hydrogen, methyl and ethyl;

R$_{11}$ is selected from the group consisting of methyl and ethyl; or

R$_{10}$ and R$_{11}$ may be associated to form —CH$_2$CH$_2$CH$_2$—;

R$_{12}$ and R$_{13}$ represent hydrogen, respectively, or oxo altogether; provided that when R$_1$, R$_2$, R$_3$, R$_4$, R$_5$ and R$_6$ represent hydroxy, hydrogen, hydrogen, hydroxy, hydroxymethyl and methyl, respectively, R is not hydrogen or methyl and R$_8$ is not hydrogen; and provided that when R$_1$ is hydroxy, R$_2$ is hydrogen, R$_3$ and R$_4$ form —OC(CH$_3$)$_2$OCH$_2$— together with R$_5$, and R$_6$ is methyl, R is not methyl.

2. A process of manufacturing an asiatic acid derivative of formula V or a pharmaceutically acceptable salt or ester thereof, which comprises reacting a compound of formula III with a compound of formula IV in the presence of a base,

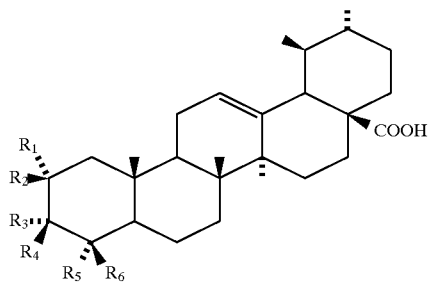

III wherein:

R$_1$ is selected from the group consisting of hydrogen, hydroxy, methyl, ethyl, methoxy, ethoxy, vinyl, ethynyl, cyano, azaide, methanesulfonyloxy, phenylthio, and (methylthio) thiocarbonyloxy, wherein said hydroxy may be protected by acetyl or benzyl;

R$_2$ is selected from the group consisting of hydrogen, hydroxy, methoxy, and ethoxy, wherein said hydroxy may be protected by acetyl or benzyl; or R$_1$ and R$_2$ may form oxo altogether;

R$_3$ is selected from the group consisting of hydrogen, hydroxy, vinyl, methyl, and ethyl, wherein said hydroxy may be protected by acetyl or benzyl;

R$_4$ is selected from the group consisting of hydrogen, methyl, ethyl, vinyl, and hydroxy, wherein said hydroxy may be protected by acetyl or benzyl; or R$_2$ and R$_4$ may form epoxy altogether; or R$_3$ and R$_4$ may form oxo altogether;

R$_5$ is selected from the group consisting of methyl, hydroxymethyl where hydroxy may be protected by acetyl or benzyl, tert-butyldimethylsilyloxymethyl, and carboxyl; or R$_4$ and R$_5$ may form —OC(CH$_3$)$_2$OCH$_2$— altogether;

R$_6$ is selected from the group consisting of hydrogen and methyl;

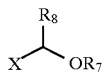

IV wherein:

R$_8$ is hydrogen, methyl, or ethyl; R$_9$ is methyl, ethyl, octyl, benzyl, methoxymethyl, or methoxyethyl; X is halogen, mesyloxy, or toxyloxy;

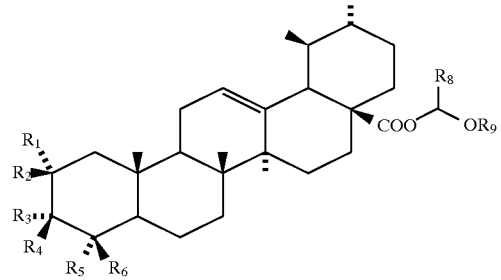

V wherein:

R$_1$ to R$_6$ and R$_8$ and R$_9$ are the same as described above.

3. A process of manufacturing an asiatic acid derivative of formula VII or a pharmaceutically acceptable salt or ester thereof, which comprises reacting a compound of formula III with a compound of formula VI in the presence of an acid catalyst,

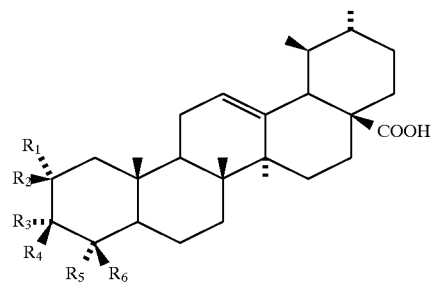

III wherein:

R$_1$ is selected from the group consisting of hydrogen, hydroxy, methyl, ethyl, methoxy, ethoxy, vinyl, ethynyl, cyano, azaide, methanesulfonyloxy, phenylthio, and (methylthio) thiocarbonyloxy, wherein said hydroxy may be protected by acetyl or benzyl;

R$_2$ is selected from the group consisting of hydrogen, hydroxy, methoxy, and ethoxy, wherein said hydroxy may be protected by acetyl or benzyl; or R$_1$ and R$_2$ may form oxo altogether;

R$_3$ is selected from the group consisting of hydrogen, hydroxy, vinyl, methyl, and ethyl, wherein said hydroxy may be protected by acetyl or benzyl;

R$_4$ is selected from the group consisting of hydrogen, methyl, ethyl, vinyl, and hydroxy, wherein said hydroxy may be protected by acetyl or benzyl; or R$_2$ and R$_4$ may form epoxy altogether; or R$_3$ and R$_4$ may form oxo altogether;

R$_5$ is selected from the group consisting of methyl, hydroxymethyl where hydroxy may be protected by acetyl or benzyl, tert-butyldimethylsilyloxymethyl, carboxyl, carboxylester, carboxylamide, and aldehyde; or R$_4$ and R$_5$ may form —OC(CH$_3$)$_2$OCH$_2$— altogether;

R$_6$ is selected from the group consisting of hydrogen and methyl;

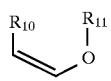
VI wherein:
R$_{10}$ is hydrogen, methyl, or ethyl; R$_{11}$ is methyl or ethyl; and R$_{10}$ and R$_{11}$ may be associated to form —CH$_2$CH$_2$CH$_2$—;

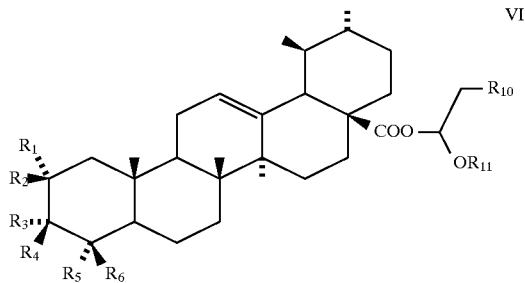
VII wherein:
R$_1$ to R$_6$ and R$_{10}$ and R$_{11}$ are the same as described above.

4. A dermatological composition comprising:
(i) an asiatic acid derivative of formula I

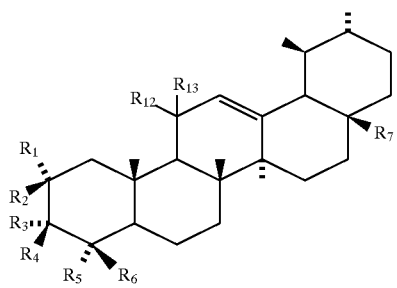
I or a pharmaceutically acceptable salt or ester thereof, wherein:
R$_1$ is selected from the group consisting of hydrogen, hydroxy, methyl, ethyl, methoxy, ethoxy, vinyl, ethynyl, cyano, azaide, methanesulfonyloxy, phenylthio, and (methylthio) thiocarbonyloxy, wherein said hydroxy may be protected by acetyl or benzyl;
R$_2$ is selected from the group consisting of hydrogen, hydroxy, methoxy, and ethoxy, wherein said hydroxy may be protected by acetyl or benzyl; or
R$_1$ and R$_2$ may form oxo altogether;
R$_3$ is selected from the group consisting of hydrogen, hydroxy, vinyl, methyl, and ethyl, wherein said hydroxy may be protected by acetyl or benzyl;
R$_4$ is selected from the group consisting of hydrogen, methyl, ethyl, vinyl, and hydroxy, wherein said hydroxy may be protected by acetyl or benzyl; or
R$_2$ and R$_4$ may form epoxy altogether; or
R$_3$ and R$_4$ may form oxo altogether;
R$_5$ is selected from the group consisting of methyl, hydroxymethyl where hydroxy may be protected by acetyl or benzyl, tert-butyldimethylsilyloxymethyl, carboxyl, carboxylester, carboxylamide, and aldehyde; or
R$_4$ and R$_5$ may form —OC(CH$_3$)$_2$OCH$_2$— altogether;
R$_6$ is selected from the group consisting of hydrogen and methyl;
R$_7$ is selected from the group consisting of —CH$_2$COOR, —COOR, hydroxymethyl where hydroxy may be protected by acetyl or benzyl, methanesulfonyloxymethyl, and cyanomethyl wherein:
R is hydrogen, methyl, CH(OR$_9$)R$_8$, CH(OR$_{11}$)CH$_2$R$_{10}$, or glucosyl or rhamnosyl where hydroxy may be protected by acetyl or benzyl;
R$_8$ is selected from the group consisting of hydrogen, methyl and ethyl;
R$_9$ is selected from the group consisting of methyl, ethyl, octyl, benzyl, methoxymethyl, and methoxyethyl;
R$_{10}$ is selected from the group consisting of hydrogen, methyl and ethyl;
R$_{11}$ is selected from the group consisting of methyl and ethyl; or
R$_{10}$ and R$_{11}$ may be associated to form —CH$_2$CH$_2$CH$_2$—;
R$_{12}$ and R$_{13}$ represent hydrogen, respectively, or oxo altogether; provided that when R$_1$, R$_2$, R$_3$, R$_4$, R$_5$ and R$_6$ represent hydroxy, hydrogen, hydrogen, hydroxy, hydroxymethyl and methyl, respectively, R is not hydrogen or methyl and R$_8$ is not hydrogen; and provided that when R$_1$ is hydroxy, R$_2$ is hydrogen, R$_3$ and R$_4$ form —OC(CH$_3$)$_2$OCH$_2$— together with R$_5$, and R$_6$ is methyl, R is not methyl; and
(ii) a pharmaceutically acceptable carrier.

* * * * *